US009580688B2

(12) United States Patent
Atala et al.

(10) Patent No.: US 9,580,688 B2
(45) Date of Patent: *Feb. 28, 2017

(54) KIDNEY STRUCTURES AND METHODS OF FORMING THE SAME

(75) Inventors: Anthony Atala, Winston-Salem, NC (US); James J. Yoo, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 554 days.

This patent is subject to a terminal disclaimer.

(21) Appl. No.: 12/618,338

(22) Filed: Nov. 13, 2009

(65) Prior Publication Data

US 2010/0112062 A1 May 6, 2010

Related U.S. Application Data

(63) Continuation-in-part of application No. 12/134,813, filed on Jun. 6, 2008.

(60) Provisional application No. 60/942,716, filed on Jun. 8, 2007, provisional application No. 61/199,344, filed on Nov. 14, 2008.

(51) Int. Cl.
| | |
|---|---|
| A01N 63/00 | (2006.01) |
| A01N 65/00 | (2009.01) |
| A61K 9/14 | (2006.01) |
| C12N 5/071 | (2010.01) |
| A61K 35/22 | (2015.01) |
| A61K 35/12 | (2015.01) |

(52) U.S. Cl.
CPC ............ *C12N 5/0686* (2013.01); *A61K 35/22* (2013.01); *A61K 35/12* (2013.01); *C12N 2500/02* (2013.01)

(58) Field of Classification Search
CPC . C12N 5/0686; C12N 5/0685; A61L 27/3891; A61L 27/3839; A61L 27/3804
USPC ...................................... 424/93.7
See application file for complete search history.

(56) References Cited

U.S. PATENT DOCUMENTS

| | | |
|---|---|---|
| 3,463,158 A | 8/1969 | Schmitt |
| 4,182,339 A | 1/1980 | Hardy, Jr. |
| 4,377,513 A | 3/1983 | Sugimoto et al. |
| 4,458,678 A | 7/1984 | Yannas et al. |
| 4,520,821 A | 6/1985 | Schmidt et al. |
| 4,594,407 A | 6/1986 | Nyilas |
| 4,769,037 A | 9/1988 | Midcalf |
| 4,963,489 A | 10/1990 | Naughton et al. |
| 4,996,154 A | 2/1991 | Gabriels, Jr. |
| 5,032,508 A | 7/1991 | Naughton et al. |
| 5,085,629 A | 2/1992 | Goldberg |
| 5,092,886 A | 3/1992 | Dobos-Hardy |
| 5,160,490 A | 11/1992 | Naughton et al. |
| 5,224,953 A | 7/1993 | Morgentaler |
| 5,261,898 A | 11/1993 | Polin |
| 5,376,376 A | 12/1994 | Li |
| 5,429,674 A | 7/1995 | Lamers |
| 5,429,938 A | 7/1995 | Humes |
| 5,433,996 A | 7/1995 | Kranzler |
| 5,443,950 A | 8/1995 | Naughton et al. |
| 5,480,436 A | 1/1996 | Bakker |
| 5,514,378 A | 5/1996 | Mikos |
| 5,516,680 A | 5/1996 | Naughton et al. |
| 5,545,131 A | 8/1996 | Davankov |
| 5,549,674 A | 8/1996 | Humes et al. |
| 5,567,612 A | 10/1996 | Vacanti et al. |
| 5,613,982 A | 3/1997 | Goldstein |
| 5,654,273 A | 8/1997 | Gallo |
| 5,686,289 A | 11/1997 | Humes et al. |
| 5,709,854 A | 1/1998 | Griffith-Cima et al. |
| 5,716,404 A | 2/1998 | Vacanti |
| 5,750,329 A | 5/1998 | Quinn et al. |
| 5,759,830 A | 6/1998 | Vacanti et al. |
| 5,762,966 A | 6/1998 | Knapp, Jr. |
| 5,766,618 A | 6/1998 | Laurencin |
| 5,770,193 A | 6/1998 | Vacanti et al. |
| 5,770,417 A | 6/1998 | Vacanti et al. |
| 5,800,537 A | 9/1998 | Bell |
| 5,851,833 A | 12/1998 | Atala |
| 5,855,610 A | 1/1999 | Vacanti et al. |
| 5,858,721 A | 1/1999 | Naughton et al. |
| 5,863,531 A | 1/1999 | Naughton et al. |
| 5,916,265 A | 6/1999 | Hu |
| 5,947,893 A | 9/1999 | Agrawal |
| 5,952,226 A | 9/1999 | Aebischer et al. |
| 5,957,972 A | 9/1999 | Williams et al. |
| 5,962,325 A | 10/1999 | Naughton et al. |
| 5,967,972 A | 10/1999 | Santilli et al. |

(Continued)

FOREIGN PATENT DOCUMENTS

| | | |
|---|---|---|
| CN | 1 044 496 A | 8/1990 |
| DE | 19919625 A1 | 11/2000 |

(Continued)

OTHER PUBLICATIONS

Kreft et al 2002, Infection and Immunity 70:2660-2656.*
Satchell SC et al. Conditionally immortalized human glomerular endothelial cells expressing fenestrations in response to VEGF. Kidney International. 2006; 69: 1633-1640.
Kempson SA et al. Proximal tubule characteristics of cultured human renal cortex epithelium. J Lab Clin Med. Mar. 1989; 113(3): 285-96. Abstract.
Yamaleyeva LM et al. Cell therapy with human renal cell cultures containing erythropoietin-positive cells improves chronic kidney injury. Stem Cells Translational Medicine. 2012; 1: 373-383.
Guimaraes-Souza NK et al. In vitro reconstitution of human kidney structures for renal cell therapy. Nephrology Dialysis Transplantation. 2012; 27: 3082-3090.

(Continued)

Primary Examiner — Christopher M Babic
Assistant Examiner — Kelaginamane T Hiriyanna
(74) Attorney, Agent, or Firm — Myers Bigel, P.A.

(57) ABSTRACT

Provided herein are isolated populations of kidney cells harvested from differentiated cells of the kidney, wherein cells have been expanded in vitro, and methods of use thereof. The cells may be provided in a three dimensional matrix for culturing in vitro and/or implanting in vivo. Methods of seeding cells onto the matrix are also provided.

19 Claims, 22 Drawing Sheets

(56) References Cited

U.S. PATENT DOCUMENTS

Figure 1:
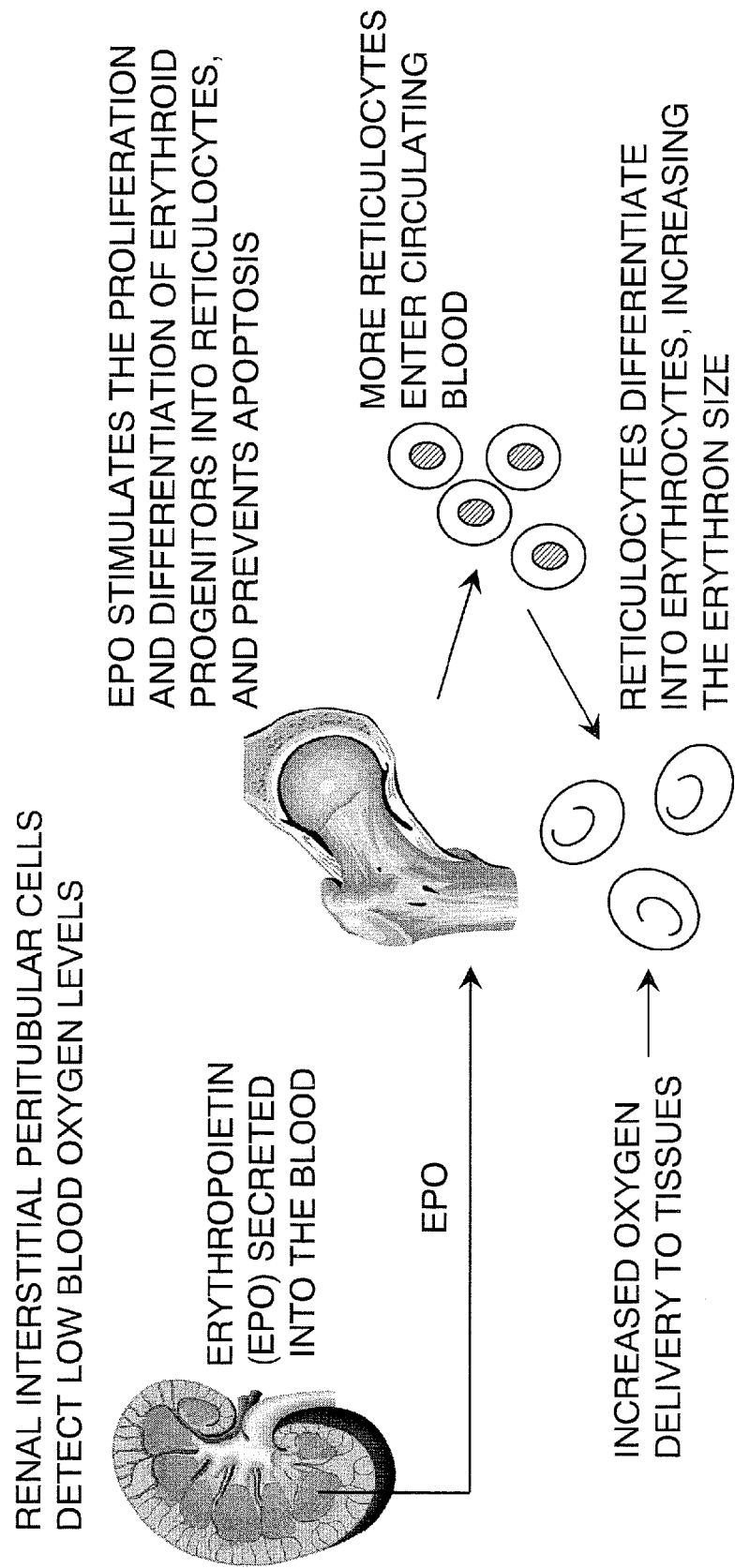

| | | | |
|---|---|---|---|
| 5,994,127 | A | 11/1999 | Selden et al. |
| 6,018,024 | A | 1/2000 | Seubert et al. |
| 6,060,270 | A | 5/2000 | Humes |
| 6,140,039 | A | 10/2000 | Naughton |
| 6,171,344 | B1 | 1/2001 | Atala |
| 6,368,859 | B1 | 4/2002 | Atala |
| 6,376,244 | B1 | 4/2002 | Atala |
| 6,410,320 | B1 * | 6/2002 | Humes .......................... 435/369 |
| 6,576,019 | B1 | 6/2003 | Atala |
| 6,638,859 | B2 | 10/2003 | Sneh et al. |
| 6,673,339 | B1 | 1/2004 | Atala et al. |
| 6,747,002 | B2 | 6/2004 | Cheung et al. |
| 6,777,205 | B1 | 8/2004 | Carcagno et al. |
| 6,784,154 | B2 | 8/2004 | Westenfelder |
| 7,326,570 | B2 | 2/2008 | Nigam et al. |
| 2002/0150604 | A1 | 10/2002 | Yi et al. |
| 2003/0180289 | A1 | 9/2003 | Foster et al. |
| 2004/0167634 | A1 | 8/2004 | Atala et al. |
| 2005/0002915 | A1 | 1/2005 | Atala et al. |
| 2005/0002919 | A1 | 1/2005 | Brenner et al. |
| 2005/0136042 | A1 | 6/2005 | Betz et al. |
| 2007/0059293 | A1 | 3/2007 | Atala |
| 2007/0078084 | A1 | 4/2007 | Kishore et al. |
| 2007/0116679 | A1 | 5/2007 | Atala |
| 2007/0128174 | A1 | 6/2007 | Kleinsek et al. |

FOREIGN PATENT DOCUMENTS

| | | |
|---|---|---|
| EP | 0194192 | 11/1989 |
| EP | 0984062 A1 | 8/2000 |
| EP | 1 548 031 A1 | 6/2005 |
| GB | 2011274 | 7/1979 |
| JP | 57 040411 A | 3/1982 |
| KR | 2001 0026239 A | 4/2001 |
| SU | 1034717 | 8/1983 |
| WO | WO 88/03785 | 6/1988 |
| WO | WO 89/01967 | 3/1989 |
| WO | WO 90/02796 | 3/1990 |
| WO | WO 90/12796 | 3/1990 |
| WO | WO 90/12604 | 11/1990 |
| WO | WO 91/09625 | 7/1991 |
| WO | WO 92/15259 | 9/1992 |
| WO | WO 93/07913 | 4/1993 |
| WO | WO 95/11048 | 4/1995 |
| WO | WO 95/24873 | 9/1995 |
| WO | WO 96/08213 | 3/1996 |
| WO | WO 96/09372 | 3/1996 |
| WO | WO 96/31232 | 10/1996 |
| WO | WO 96/40175 | 12/1996 |
| WO | WO 98/06445 | 2/1998 |
| WO | WO 98/09582 | 3/1998 |
| WO | WO 98-09582 A | 3/1998 |
| WO | WO 98/46165 | 10/1998 |
| WO | WO 99/00152 | 1/1999 |
| WO | WO 99/22677 | 5/1999 |
| WO | WO 99/22781 | 5/1999 |
| WO | WO 00/66036 | 11/2000 |
| WO | WO 00/67672 | 11/2000 |
| WO | WO 01/17572 | 3/2001 |
| WO | WO 01/48153 | 7/2001 |
| WO | WO 01/49210 | 7/2001 |
| WO | WO 01/49827 A1 | 7/2001 |
| WO | WO 02/20034 A1 | 3/2002 |
| WO | WO 02-061053 A1 | 8/2002 |
| WO | WO 02/088338 A2 | 11/2002 |
| WO | WO 2004/009768 A2 | 1/2004 |
| WO | WO 2005/012508 A1 | 2/2005 |
| WO | WO 2007-035843 A2 | 3/2007 |
| WO | WO 2008-045498 A1 | 4/2008 |

OTHER PUBLICATIONS

International Search Report and Written Opinion, PCT/US09/64421, mailed Feb. 19, 2010.

"Contact," in Webster's College Dictionary 293 (Robert B. Costello ed., Random House 1991).

Alberti, et al, "What's in the pipeline about bladder reconstructive surgery?" Int. J. Artif. Organs 27: 737-743, (2004).

Aldskogius, et al. "Strategies for repair of the deafferented spinal cord", Brain Res Rev 20: 301-308, (2002).

Amann, et al., "Cardiac remodeling in experimental renal failure—an immunohistochemical study", Nephrology Dial Transplant, 13: 1958-1966, (1998).

Anglani, et al., "The renal stem cell system in kidney repair and regeneration", Frontiers in Bioscience, 13: pp. 6395-6405, (2008).

Answers.com definition of "vascular." Accessed online Dec. 5, 2005/ p. 1.

Ashkar, et al., "Regulation of Gluconeogenesis in Swine Kidney Proximal Tubule Cells," Molecular and Cellular Biochemistry, 87:105-118 (1989).

Atala et al., "Injectable Alginate Seeded with Chondrocytes as Potential Treatment for Vesicoureteral Reflux," The Journal of Urology, vol. 150, 745-7 (Aug. 1993).

Atala, "Tissue Engineering for Bladder Substitution", World J. Urol., vol. 18: 364-370, (2000).

Atala, A. et al., "Formation of Urothelial Structures in Vivo From Dissociated Cells Attached to Biodegradable Polymer Scaffolds in Vitro," *The Journal of Urology,* vol. 148, 648-662 (Aug. 1992).

Atala, A., et al., "Pediatric urology—future perspectives," In: Clinical Urology, edited by R. J. Krane M.B. Siroky and J. M. Fitzpatrick (Philadelphia: J.B. Lippincott, 1994), pp. 507-524.

Atala, et al., "Implantation in Vivo and Retrieval of Artificial Structures Consisting of Rabbit and Human Urothelium and Human Bladder Muscle," The Journal of Urology, vol. 150, 608-612 (Aug. 1993).

Atala, et al., "Renal Cell growth in vivo after attachment to biodegradable polymer scaffolds," J Urology 153:4, (1995).

Atala A. Tissue engineering for the replacement of organ function in the genitourinary system. American Journal of Transplantation. 4(Suppl. 6): 58-73 (2004).

Bazeed, et al., "New treatment for urothelial structures," Urology 21:53-57 (1983).

Ben-Ze'ev, A. et al., "Cell-cell and Cell-matrix Interactions Differentially Regulate the Expression of Hepatic and Cytoskeletal Genes in Primary Cultures of Rat Hepatocytes," PNAS, vol. 85, 2161-2165 (Apr. 1988).

Bissell, D. et al., "Interactions of Rat Hepatocytes with Type IV Collagen, Fibronectin and Laminin Matrices, Distinct Matrix-controlled Modes of Attachment and Spreading," European Journal of Cell Biology, vol. 40, 72-78 (1986).

Boogaard, P.J. et al., "Renal Proximal Tubular Cells in Suspension or in Primary Culture as In Vitro Models to Study Nephrotoxicity," (ABST) Chem. Biol. Interact, 76(3):251-291 (1990).

Burke, J.F. et al., "Successful use of physiologically acceptable artificial skin in the treatment of an extensive burn injury," Ann. Surg., 194:413 (1981).

Burke, J.F., "The Effects of the Configuration of an Artificial Extracellular Matrix on the Development of a Functional Dermis," The Role of Extracellular Matrix in Development, Alan R. Liss, Inc.. eds. (NY). 351-55 (1984).

Castro, R.F. et al, "Failure of bone marrow cells to transdifferentiate into neural cells in vitro", Science. 297: 1299, (2002).

Chlapowski, F.J. "Long-term growth and maintenance of stratified rat urothelium in vitro," Cell Tissue Kinet. 22: 245-257 (1989).

Cilento, B.G. et al., "Phenotypic and Cytogenetic Characterization of Human Bladder Urothelia Expanded in Vitro," The Journal of Urology, vol. 152, 665-70 (Aug. 1994).

Cima, L.G. et al., "Hepatocyte culture on biodegradable polymeric substrates," Biotechnol. Bioeng. 38. 145-158 (1991).

Courjault-Gautier, F. et al., "Consecutive use of Hormonally Defined Serum-free Media to Establish Highly Differentiated Human Renal Proximal Tubule Cells in Primary Culture," (ABST) J. Am. Soc. Nephrol., 5(11): 1949-1963 (May 1995).

Craig, P.H., et al., "A biological comparison of polyglactin 910 and polyglycolic acid synthetic absorbable sutures," Surg. 141: 1-10 (1975).

(56) References Cited

OTHER PUBLICATIONS

Culliton, B.J., "Gore Tex Organoids and Genetic Drugs," Science, Vol, 246, 747-9 (Nov. 10, 1989).
Da Silva, C.F. et al., "An In Vivo Model to Quantify Motor and Sensory Peripheral Nerve Regeneration Using Bioresorbable Nerve Guide Tubes," Brain Research, vol. 342, 307-15 (1985).
Daley G.Q. at al., "Realistic prospects for stem cell therapeutics.", Ficmatol.: 398-418, (2003).
Davis, G.E. et al., "Human Amnion Membrane Serves as a Substratum for Growing Axons in Vitro and in Vivo," Science, vol. 236, 1106-1109 (May 29, 1987).
Ebata, H. et al., "Liver Regeneration Utilizing Isolated Hepatocytes Transplanted into the Rat Spleen," Surg Forum, vol. 29, 338-40 (1978).
Fontaine, M. et al., "Transplantation of Genetically Altered Hepatocytes Using Cell-Polymer Constructs," Transplantation Proceedings, vol. 25, No. 1, 1002-4 (Feb. 1993).
Fournier, N. et al., "Biological Molecule-impregnated Polyester: An In Vivo Angiogenesis Study," (ABST) Biomaterials, 17(17):1659-1665 (1996).
Freeman, M.R., et al., "Induction and segregation of glial intermediate filament expression in the RT4 family of peripheral nervous system cell lines," Proc. Natl. Acad. Sci. USA 84.5808 (1987).
Genestie, et al., "Polarity and Transport Properties of Rabbit Kidney Proximal Tubule Cells on Collagen IV-coated Porous Membranes," (ABST) Am. J. Physiol. 269(1): pt, 2, 22-30 (Jul. 1995).
Gilbert, J. et al., "Cell Transplantation of Genetically Altered Cells on Biodegradable Polymer Scaffolds in Syngeneic Rats," Transplantation, vol. 56, No. 2, 423-427 (Aug. 1993).
Graham, N.B.,. "Hydrogels: Their Future, Part I", Medical Device Technology, 18-22 (Jan./Feb. 1998).
Graham, n. B., "Hydrogels: Their Future, Part II", Medical Device Technology, 22-25 (Apr. 1998).
Green, H. et al., "Growth of cultured human epidermal cells into multiple epithelia suitable for grafting,", Proc. Natl. Acad. Sci. 76: 5665-5668, (1979).
Grupp C et al. "Isolation and characterization of the lower portion of the thin limb of Henle in primary culture.", Am J Physiol., 274: F775-F782, (1998).
Guo, et al., "Cellular maintenance and repair of the kidney", Annu. Rev. Physiol., 72: 357-376, (2010).
Hammerman, M.R., "Growing kidneys", Current opinion Nephrology and Hypertension, 10: 13-17 (2001).
Held, P.K. et al., "In vivo genetic selection of renal proximal tubules", Molecular Therapy, vol. 13, No. 1, pp. 49-58, (2006).
Hendren, W.H. et al., "Bladder mucosa graft for construction of the male urethra," J. Pediatr. Surg. 21:189-192 (1986).
Henry, E.W. et al., "Nerve Regeneration Through Biodegradable Polyester Tubes," Experimental Neurology, vol. 90, 652-76 (1985).
Hoffman, et al., "Biodegradable synthetic polymer scaffolds for reinforcement of albumin protein solders used for laser-assisted tissue repair.", Biomed Sci Instrum. 2002;38: 53-58, Abstract.
Humes, H.D. et al., "Initial clinical results of the bioartificial kidney containing human cells in ICU patients with acute renal failure", Kidney International, vol. 66, pp. 1578-1588 (2004).
Humes, H.D. et al., "Replacement of renal function in uremic animals with a tissue-engineered kidney", Nature, vol. 17, pp. 451-455, (1999).
Humes, H.D. et al., "Effects of Transforming Growth Factor-beta, Transforming Growth Factor-alpha, and Other Growth Factors on Renal Proximal Tubule Cells," Laboratory Investigation, 64(4):538-545 (1991).
Humes, H.D. et al., "Tubulogenesis From Isolated Single Cells of Adult Mammalian Kidney-Clonal Analysis With a Recombinant Retrovirus," (ABST) Am. J. of Physiology—Renal Fluid and Electrolyte Physiology, 40(1): 42-49, (Jul. 1996).
Humphreys, B.D. et al., "Mesenchymal stem cells in acute kidney injury", Annu. Rev. Med. 59: 311-325, (2008).
Ingber, D. et al., "Endothelial Growth Factors and Extracellular Matrix Regulate DNA Synthesis Through Modulation of Cell and Nuclear Expansion," In Vitro Cellular & Developmental Biology, vol. 23, No. 5, 387-94 (May 1987).
International Search Report, PCT/US00/33891, issued Mar. 26, 2001.
Jarad, G. et al., "Update on the glomerular filtration barrier", Curr. Opin. Nephrol Hypertens, 15: 226-232, (2009).
Jauregui, H.O. et al., "Attachment and Long Term Survival of Adult Rat Hepatocytes in Primary Monolayer Cultures: Comparison of Different Substrata and Tissue Culture Media Formulations," in Vitro Cellular & Developmental Biology, vol. 22, No. 1, 13-22 (Jan. 1986).
Joraku, A. et al., "In vitro generation of three-dimensional renal structures", Methods, 47: 129-133, (2009).
Kaufman, J.M. et al., "Compensatory adaptation of structure and function following progressive renal ablation", Kidney International, vol. 6, pp. 10-17, (1974).
Kim, S-S et al., "Kidney tissue reconstruction by fetal kidney cell transplantation: Effect of gestation stage of fetal kidney cells", Stem Cells, 25: 1393-1401, (2007).
Kirker-Head, C., "Recombinant Bone Morphogenetic Proteins: Novel Substances for Enhancing Bone Healing," Vet. Surg. vol. 24: 408-419, (1995).
Kirschstein R et al. Can stem cells repair a damaged heart? in Stem cells: scientific progress and future research directions. pp. 87-92, (2001).
Kucic, T. et al., "Mesenchymal stromal cells genetically engineered to overexpress IGF-I enhance cell-based gene therapy of renal failure-induced anemia", Am. J. Physiol. Renal Physiol., 295: F488-F496, (2008).
Laemmil, U.K., "Cleavage of structural proteins during assembly of the head of bacteriophage T4," Nature (London) 227:680-685 (1970).
Langer, R. and Moses, M., "Biocompatible Controlled Release Polymers for Delivery of Polypeptides and Growth Factors," Journal of Cellular Biochemistry, vol. 45, 340-5 (1991).
Laurencin, C.T., "A Highly Porous 3 Dimensional Polyphosphazene Polymer Matrix for Skeletal Tissue Regeneration" J. Biomed. Mater. Res., vol. 30:133-138 (1996).
Lin, F. et al., "Intrarenal cells, not bone marrow-derived cells, are the major source for regeneration in postischemic kidney", The Journal of Clinical Investigation, vol. 115, No, 7, pp. 1756-1764, (2005)
Marshall, D. et al., "Increasing renal mass improves survival in anephric rats following metanephros transplantation", Experimental Physiology, 92.1: 263-271, (2007).
Mezey, et al., Comment on "Failure of bone marrow cells to transdifferentiate into neural cells in vitro", Science 299: 1184b-1184c, (2003).
Michalopoulos, G. and Pitot, H.C., "Primary Culture of Parenchymal Liver Cells on Collagen Membranes," Experimental Cell Research, vol. 94, 70-78 (1975).
Mooney, D. and Vacanti, J., "Tissue Engineering Using Cells and Synthetic Polymers," Transplantation Reviews, vol. 7. No. 3. 153-62 (Jul. 1993).
Naughton, B.A. et al., "Long-term Growth of Rat Bone Marrow Cells in a Three-dimensional Matrix," The Anatomical Record, vol. 218, 97A (1987).
Newsome, "Yet another role for mesenchmyal stem cells?", Transplantation, vol. 85, No. 11, pp. 1548-1549, (2008).
Nikolovski, J. et al., "Design Engineering of a Bioartificial Renal Tubule Cell Therapy Device," Cell Transplantation, vol. 8, 351-64 (1999).
Oberpenning, F. et al. "De novo reconstitution of a functional mammalian urinary bladder by tissue engineering", Nat Biotech 17: 149-155, (1999).
O'Connor, N. et al., "Grafting of Burns with Cultured Epithelium Prepared from Autologous Epidermal Cells." The Lancet, 75-78 (Jan. 10, 1981).
Ogawa Y., "Injectable microcapsules prepared with biodegradable poly (alpha-hydroxyl) acids for prolonged release of drugs.", J Biomater Sci Polym Ed., 8(5): 391-409, (1997), Abstract only.

(56) References Cited

OTHER PUBLICATIONS

Ormrod, D. et al., "Experimental Uremia: description of a model producing varying degrees of stable uremia", Nephron, 26: 249-254, (1980).
Patschan, D. et al., "Therapeutic use of stem and endothelial progenitor cells in acute renal injury: ça ira", Current Opinion in Pharmacology, 6: 176-183, (2006).
Platt, R. et al., "Experimental renal failure", Department of Medicine, University of Manchester, pp. 217-231, (1952).
Pope, IV, J. C. et al., "The ontogeny of canine small intestine submucosa regenerated bladder," J Urology 158:1105-1110, 1997.
Powe, N.R. et al. Public health surveillance of CKD: principles, steps and challenges. American Journal of Kidney Diseases. 53(3) Suppl. 3; S37-S45 (Mar. 2009).
Prodromidi E.I. Bone Marrow-derived cells contributed to podocyte regeneration and amelioration of renal disease in a mouse model of alport syndrome. Stem Cells. 24: 2448-2455 (2006).
Puelacher, W.C. et al., "Tissue-engineered Growth of Cartilage: The Effect of Varying the Concentration of Chondrocytes Seeded Onto Synthetic Polymer Matrices," Int. J. Oral Maxillofac. Surg., vol. 23, 49-53 (1994).
Ransley, P.G., et al., "Autologous bladder mucosa graft for urethral substitution," Br. J. Urol. 58:331-333 (1986).
Reid, L.M. et al., "Long-term Cultures of Normal Rat Hepatocytes on Liver Biomatrix," Annals New York Academy of Sciences, 70-6 (1980).
Reznikoff, C.A. et al., "Growth kinetics and differentiation in vitro of normal human uroepithelial cells on collagen gel substrates in defined medium," J. Cell Physiol. 131:285-301 (1987).
Rhine, W.D. et al., "Polymers for Sustained Macromolecule Release: Procedures to Fabricate Reproducible Delivery Systems and Control Release Kinetics," Journal of Pharmaceutical Sciences, vol. 69, No. 3, 265-70 (Mar. 1980).
Romagnoli, G., et al., "Treatment of posterior hypospadias by the autologous graft of cultures urethral epithelium," New England J. Med. 323:527-530, (1990).
Rosen, H.B. et al., "Bioerodible Polyanhydrides for Controlled Drug Delivery," Biomaterials, vol. 4, 131-3 (Apr. 1983).
Roskams AJ et al, "Directing stem cells and progenitor cells on the stage of spinal cord injury.", Exp Neurol 193: 267-272, (2005).
Sawada, N. et al., "Effects of Extracellular Matrix Components on the Growth and Differentiation of Cultured Rat Hepatocytes," in Vitro Cellular & Developmental Biology, vol. 23, No. 4, 267-73 (Apr. 1987).
Scriven, S. D. et al., "Reconstitution of human urothelium from monolayer cultures," J Urology 158:1147-1153, 1997.
Seckel, B.R. et ai., "Nerve Regeneration through Synthetic biodegradable nerve guides: Regulation by the Target Organ," Plastic and Reconstructive Surgery, vol. 74, No. 2. 173-81 (Aug. 1984).
Shine, H.D. et al., "Cultured Peripheral Nervous System Cells Support Peripheral Nerve Regeneration Through Tubes in the Absence of Distal Nerve Stump," Journal of Neuroscience Research, vol. 14, 393-401 (1985).
Staack A et al.. "Molecular. cellular, and developmental biology of urothelium as a basis of bladder regeneration.", Differentiation 73: 121-133, (2005).
Sugimoto H. et al. Bone-marrow-derived stem cells repair basement membrane collagen defects and reverse genetic kidney disease. PNAS, 103(19); 7321-7326 (May 9, 2006).
Tachibana, M. et al., "Ureteral Replacement Using Collagen Sponge Tube Grafts," The Journal of Urology, vol. 133, 866-9 (May 1985).
Takeda, T. et al., "Hepatocyte Transplantation in Biodegradable Polymer Scaffolds Using the Dalmatian Dog Model of Hyperuricosuria," Transplantation Proceedings, vol. 27, No. 1, 635-6 (Feb. 1995).
Taub, M. et al., "Epidermal Growth Factor or Transforming Growth Factor a is Required for Kidney Tubulogenesis in Matrigel Cultures in Serum-Free Medium," Proc. Natl. Acad. Sci., 87:4002-4006 (May 1990).
Thompson, J.A. et al., "Heparin-binding Growth Factor 1 Induces the Formation of Organoid Neovascular Structures in vivo," PNAS, vol, 86, 7928-7932 (Oct. 1989).
Thompson, J.A. et al., "Implantable Bioreactors: Modern Concepts of Gene Therapy," Current Communications in Molecular Biology: Therapeutic Peptides and Proteins, Cold Spring Harbor Laboratory, eds., 143-147, (1989).
Thiiroff, J.W. et al., "Cultured Rabbit Vesical Smooth Muscle Cells for Lining of Dissolvable Synthetic Prosthesis," Urology XXI: 155-158, (1983).
Tosh D, et al, "Conversion of pancreatic cells to hepatocytes.", Biochem .Soo. Transact 30: 51-55, (2002).
Tseng, S.C.G., et al., "Correlation of specific keratins with different types of epithelial differentiation: monoclonal antibody studies," Cell 30: 361-372 (1982).
Urry, D. and Pattanaik, A., "Elastic Protein-based Materials in Tissue Reconstruction," Annals New York Academy of Sciences, vol. 831,32-46 (Dec. 31, 1997).
Uyama, S. et al., "Delivery of Whole Liver-equivalent Hepatocyte Mass Using Polymer Devices and Hepatotrophic Stimulation," Transplantation, vol. 55, No. 4, 932-5 (Apr. 1993).
Vacanti, J.P. "Beyond Transplantation," Arch. Surg. 123: 545-549 (1988).
Vacanti, J.P. et al., "Selective cell transplantation using bioabsorbable artificial polymers as matrices," J. Ped. Surg. 23:3 (1988).
Vacanti, C.A. et al., "Synthetic polymers seeded with chondrocytes provide a template for new cartilage formation," J. Plast. Reconstr. Surg. 88:753-759 (1991).
Van der Kwast, T.H. et al., "Establishment and characterization of long term primary mouse urothelial cell cultures," Urol. Res. 17:289-293 (1989).
Yokoo T. et al. Generation of a transplantable erythropoietin-producer derived from human mesenchymal stem cells. Transplantation. 85(11): 1654-1658 (Jun. 15, 2008).
Yoo, J.J. et al., "Cartilage rods as potential material for penile reconstruction in ambiguous or inadequate genitalia," Pediatrics (suppl),. 100(3): 576, 1997.
Yoo, J. et al., "Creation of functional kidney structures with excretion of urine-like fluid in vivo," Pediatrics (suppl), 98(s): 605, 1996.
Yoo, J. J., "A novel gene delivery system using urothelial tissue engineered neo-organs," J Urology 158: 1066-1170, 1997.
Zdrahala, R.J., "Small Caliber Vascular Grafts. Part I: State of the Art" J. Biomater. Appl., vol. 10: 309-329 (Apr. 1996).
Zimmermann, U. et al., "Hydrogel-Based Non-Autologous Cell and Tissue Therapy.", BioTechniques, 29: 564-581 (2000).
Atala, "Tissue engineering in urologic surgery", Urologic Clinics of North America, vol. 25, No. 1, pp. 39-50, (1998).
Costa-Giomi P et al. Enhancement by hypoxia of human erythropoietin gene transcription in vitro. J Biol Chem. Jun. 25, 1990; 265(18): 1085-1088.
Bachmann S et al. Co-localization of erythropoietin mRNA and ecto-5'-nucleotidase immunoreactivity in peritubular cells of rat renal cortex indicates that fibroblasts produce erythropoietin. Journal of Histochemistry and Cytochemistry. 1993; 41(3): 335-341.
Liapis H et al. In situ hybridization of human erythropoietin in pre- and postnatal kidneys. Pediatr Pathol Lab Med. Nov.-Dec. 1995; 15(6): 875-83. Abstract p. 1-1.
Bahlmann FH et al. Erythropoietin regulates endothelial progenitor cells. Blood. Feb. 1, 2004; 103(3): 921-926.
Fandrey J. Oxygen-dependent and tissue-specific regulation of erythropoietin gene expression. Am J Physiol Integr Comp Physiol. Jun. 2004; 285: R977-R988.
Stockmann C and Fandrey J. Hypoxia-induced erythropoietin production: a paradigm for oxygen-regulated gene expression. Clinical and Experimental Pharmacology and Physiology. 2006; 33: 968-979.
Kishore BK et al. Administration of poly-D-glutamic acid induces proliferation of erythropoietin-producing peritubular cells in rat kidney. Am J Physiol Renal Physiol. Feb. 2007; 292: F749-F761.
IP Australia, Patent Examination Report No. 2, Patent Application No. 2008262333. Report issued Nov. 21, 2013, 5 pages.
Japanese Office Action, JP2010-511210, May 27, 2014.

(56) References Cited

OTHER PUBLICATIONS

Sherwood JB and Shouval D. Continuous production of erythropoietin by an established human renal carcinoma cell line: development of the cell line. Pro. Natl. Acad. Sci. USA. Jan. 1986; 83: 165-169.
Korean Office Action, KR 10-2009-7026740, Sep. 29, 2014.
Korean Office Action, KR 10-2014-7033468, Dec. 22, 2014.
Fisher JW et al. Erythropoietin production by interstitial cells of hypoxic monkey kidneys. Br J Haematol. Oct. 1996; 95(1): 27-32. Abstract.
Sikka PK and McMartin KE. Normal rat kidney proximal tubule cells in primary and multiple subcultures. In Vitro Cell Dev Biol Anim. May 1996; 32(5): 285-91. Abstract.
Kreft B et al. Polarized expression of Tamm-Horsfall protein by renal tubular epithelial cells activates human granulocytes. Infection and Immunity. May 2002; 70(5): 2650-2656.
Chinese Office Action, Chinese Patent Application No. 2013107175159; issued Jun. 25, 2015.
Schuster SJ et al. Cellular sites of extrarenal and renal erythropoietin production in anaemic rats. British Journal of Haematology. 1992; 81: 153-159.
Kurtz A et al. Renal mesangial cell cultures as a model for study of erythropoietin roduction. Proc. Natl. Acad. Sci. USA, Jul. 1983; 80: 4008-4011.
Kurtz A et al. Erythropoietin production in cultures of rat renal mesangial cells. Contributions to Nephrology, Jan. 1, 1986; 50: 175-187.
Krantz SB. Erythropoietin. Blood, Feb. 1, 1991; 77(3): 419-434.
Fandrey J and Bunn HF. In vivo and in vitro regulation of erythropoietin mRNA: measurement by competitive polymerase chain reaction. Blood. 1993; 81: 617-623.
Maxwell PH et al. Identification of the renal erythropoietin-producing cells using transgenic mice. Kidney International, 1993; 44: 1149-1162.
Turman MA and Apple CA. Human proximal tubular epithelial cells express somatostatin: regulation by growth factors and cAMP. Am J Physiol Renal Physiol, Jun. 1998; 274: 1095-1101.
Amiel GE et al. Renal therapy using tissue-engineered constructs and gene delivery. World J Urol, 2000; 18: 71-79.
Sasaki R et al. Erythropoietin: multiple physiological functions and regulation of biosynthesis. Biosci Biotechnol Biochem, 2000; 64(9): 1775-1793.
Shapiro AMJ et al. Islet transplantation in seven patients with type 1 diabetes mellitus using a glucocorticoid-free immunosuppressive regimen. N Engl J Med, Jul. 27, 2000; 343(4): 230-238.
Atala A. Tissue engineering in urology. Current Urology Reports, 2001; 2: 83-92.
Rezzani R et al. Cyclosporine A-induced toxicity in two renal cell culture models (LLC-PK1 and MDCK). The Histochemical Journal, Jan. 1, 2002; 34(1-2): 27-33.
Rinsch C et al. Delivery of erythropoietin by encapsulated myoblasts in a genetic model of severe anemia. Kidney Int'l, 2002; 62: 1395-1401.
Donnelly S. New insights into renal anemia. Canadian J of Diabetes, 2003; 27(2): 176-181.
Fisher JW. Erythropoietin: physiology and pharmacology update. Experimental Biology and Medicine, 2003; 228: 1-14.
Rossert J et al. Anemia management and the delay of chronic renal failure progression. J Am Soc Nephrol, 2003; 14: S173-S177.
Atala A. Tissue engineering for the replacement of organ function in the genitourinary system. Am J Transplantation, 2004; 4(Suppl. 6): 58-73.
Yamaguchi-Yamada M et al. Dysfunction of erythropoietin-producing interstitial cells in the kidneys of ICR-derived glomerulonephritis (ICGN) mice. J Vet Med Sci, 2005; 67(9): 891-899.
Hodges SJ and Atala A. Initial clinical results of the bioartificial kidney containing human cells in ICU patients with acute renal failure. Current Urology Reports, Feb. 2006; 7(1): 41-42.
Nangaku M. Chronic hypoxia and tubulointerstitial injury: a final common pathway to end-stage renal failure. J Am Soc Nephrol, 2006; 17: 17-25.
Plotkin MD and Goligorsky MS. Mesenchymal cells from adult kidney support angiogenesis and differentiate into multiple interstitial cell types including erythropoietin-producing fibroblasts. Am J Physiol Renal Physiol, Apr. 18, 2006; 291: F902-F912.
Shapiro AMJ et al. International trial of the Edmonton Protocol for islet transplantation. N Engl J Med, 2006; 355: 1318-30.
Bretzel RG et al. Islet cell transplantation today. Langenbecks Arch Surg, 2007; 392: 239-253.
Santa Cruz Biotechnology, Inc. Product description for Epo (H-162): sc-7956. www.scbt.com.
Search Report and Written Opinion, PCT/US2008/007161, mailed Oct. 21, 2008.
Aboushwareb T et al. Erythropoietin producing cells for potential cell therapy. World Journal of Urology. 2008; 26(4): 295-300.
Search Report and Written Opinion, PCT/US09/64418, mailed Jan. 19, 2010.
Office Action, Korean Patent Application No. 10-2009-7026740, issued Sep. 24, 2015.
Office Action, Japanese Patent Application No. 2014-198530, issued Nov. 13, 2015.
Office Action, Canadian Patent Application No. 2,688,265, issued Jan. 11, 2016.
Atala A and Lanza RP, eds. Methods of Tissue Engineering. Academic Press 2002, pp. 37 and 229.
Sikka PK and Mcmartin KE. Normal rat kidney proximal tubule cells in primary and multiple subcultures. In Vitro Cell Dev Biol Anim. May 1996; 32(5): 285-91.

\* cited by examiner

KIDNEY STRUCTURES AND METHODS OF FORMING THE SAME

RELATED APPLICATIONS

This application is a continuation-in-part and claims the benefit under 35 U.S.C. §120 of U.S. patent application Ser. No. 12/134,813, filed Jun. 6, 2008, which claims the benefit under 35 U.S.C. §119(e) of U.S. Provisional Patent Application Ser. No. 60/942,716, filed Jun. 8, 2007, the disclosure of each of which is incorporated herein by reference in its entirety.

This application also claims the benefit under 35 U.S.C. §119(e) of U.S. Provisional Patent Application Ser. No. 61/199,344, filed Nov. 14, 2008, the disclosure of which is incorporated herein by reference in its entirety.

FIELD OF THE INVENTION

The present invention is in the field of tissue regeneration for the restoration of organ function.

BACKGROUND OF THE INVENTION

Chronic renal failure is characterized by a gradual loss in kidney function, and may eventually progress to end stage renal failure, where the kidney no longer functions at a level to sustain the body. End stage renal failure is a devastating disease that involves multiple organs in affected individuals. The most common cause of end stage renal disease in the U.S. is diabetes.

One of the functions performed by the kidney is the production of erythropoietin (EPO). When the kidney is functioning properly, low tissue oxygenation in the renal interstitium stimulates the interstitial cells to produce EPO. The secreted EPO in turn stimulates red blood cell production in the bone marrow, which restores tissue oxygen tension to normal levels. Anemia caused by ineffective hematopoiesis is one of the inevitable outcomes of chronic renal failure due to the kidney's decreased ability to produce EPO. EPO has also been reported to protect against oxidative stress and apoptosis.

The kidney is the primary producer of EPO in the body and is therefore a primary target of treatment for renal failure induced anemia. Although dialysis can prolong survival for many patients with end stage renal disease, only renal transplantation can currently restore normal function. However, renal transplantation is severely limited by a critical donor shortage.

Treatments used to alleviate anemia associated with renal failure over the years include repeated transfusions of red blood cells and administration of testosterone and other anabolic steroids. However, none of these modalities has been entirely satisfactory. Patients receiving repeated transfusions are subject to iron overload, and may develop antibodies to major histocompatibility antigens. Testosterone has a minimal effect on erythropoiesis in the bone marrow, and it is associated with undesirable, virilizing side effects.

Previous efforts to mitigate anemia associated with renal failure have included the administration of purified recombinant EPO (See, e.g., U.S. Pat. No. 6,747,002 to Cheung et al., U.S. Pat. No. 6,784,154 to Westenfelder). However, the administration of recombinant EPO only elevates EPO levels in the blood temporarily, and may lead to iron deficiency. Gene therapy approaches have also been pursued, in which EPO is produced using transfected host cells (See, e.g., U.S. Pat. No. 5,994,127 to Selden et al., U.S. Pat. No. 5,952,226 to Aebischer et al., U.S. Pat. No. 6,777,205 to Carcagno et al.; Rinsch et al. (2002) Kidney International 62:1395-1401). However, these approaches involve the transfection of non-kidney cells, and require techniques such as cell encapsulation to prevent antigen recognition and immune rejection upon transplantation. Also, transfection with exogenous DNA may be unstable, and the cells may lose their ability to express EPO over time.

Renal cell-based approaches to the replacement of kidney tissue is limited by the need to identify and expand renal cells in sufficient quantities. In addition, the culturing of renal cells for the purpose of kidney tissue engineering is particularly difficult, owing to the kidney's unique structural and cellular heterogeneity. The kidney is a complex organ with multiple functions, including waste excretion, body homeostasis, electrolyte balance, solute transport, as well as hormone production.

There remains a great need for alternative treatment options to alleviate anemia and other loss of kidney function in kidney disease.

SUMMARY OF THE INVENTION

Provided herein are isolated populations of cells (e.g., mammalian, including human) comprising differentiated mammalian kidney cells, wherein said cells are harvested from mammalian kidney tissue, passaged in vitro, and, optionally, seeded onto a three dimensional matrix. In some embodiments, cells are positive for a marker selected from the group consisting of: erythropoietin (EPO), neprilysin (NEP), Tamm-Horsfall protein (THP), podocin (POD), and combinations thereof, after said passaging. In some embodiments, the population consists essentially of said differentiated mammalian kidney cells. In some embodiments, the matrix comprises neutralized collagen (e.g., type I).

In some embodiments, the mammalian kidney cells have been passaged in vitro from 1 to 20 times. In some embodiments, the mammalian kidney cells have been passaged in vitro at least 3 times. In some embodiments, the mammalian kidney cells have been passaged in vitro from 1 to 5 times.

In some embodiments, the population has been selected for EPO production (e.g., prior to having been seeded onto said matrix). Some embodiments are subject to the proviso that the cells are not transfected with an exogenous DNA encoding a polypeptide.

A composition comprising the population of cells as given above and a pharmaceutically acceptable carrier is also provided.

Further provided are methods of treating a kidney disease in a patient in need thereof, including providing a composition comprising the population of cells as given above; and administering said composition to said patient in an amount effective to treat said kidney disease. In some embodiments, the kidney disease is an anemia selected from the group consisting of: an anemia of renal failure, an anemia of end-stage renal disease, an anemia of a chemotherapy, an anemia of a radiation therapy, an anemia of chronic infection, an anemia of an autoimmune disease, an anemia of rheumatoid arthritis, an anemia of AIDS, an anemia of a malignancy, an anemia of prematurity, an anemia of hypothyroidism, an anemia of malnutrition, and an anemia of a blood disorder. In some embodiments, the administering step is carried out by implanting said composition into said patient.

Also provided are methods of producing a three dimensional seeded matrix of differentiated kidney cells, including providing differentiated kidney cells; and passaging the differentiated kidney cells, wherein the cells are positive for a marker selected from the group consisting of: erythropoietin (EPO), neprilysin (NEP), Tamm-Horsfall protein (THP), podocin (POD), and combinations thereof, after said passaging; seeding said differentiated kidney cells onto a three dimensional matrix; and then solidifying said collagen matrix. In some embodiments, the differentiated kidney cells are selected for EPO production. In some embodiments, the passaging is carried out from 1 to 20 times. In some embodiments, the matrix comprises neutralized collagen (e.g., type I).

Methods of treating a kidney disease resulting in decreased EPO production in a patient in need thereof are also provided, including providing a composition comprising an isolated population of EPO producing cells in a three dimensional matrix; and administering said composition to said patient, whereby said EPO producing cells produce EPO in vivo. In some embodiments, the administering step is carried out by implanting said composition into the kidney of said patient. Some embodiments are subject to the proviso that the EPO producing cells are not transfected with an exogenous DNA encoding a polypeptide. In some embodiments, the kidney disease is an anemia selected from the group consisting of: an anemia of renal failure, an anemia of end-stage renal disease, an anemia of a chemotherapy, an anemia of a radiation therapy, an anemia of chronic infection, an anemia of an autoimmune disease, an anemia of rheumatoid arthritis, an anemia of AIDS, an anemia of a malignancy, an anemia of prematurity, an anemia of hypothyroidism, an anemia of malnutrition, and an anemia of a blood disorder. In some embodiments, the matrix comprises neutralized collagen (e.g., type I).

Another aspect of the present invention is the use of the methods as described herein for the preparation of a composition or medicament for use in treatment or for carrying out a method of treatment as described herein (e.g., for treating a kidney disease or other ailment resulting in decreased EPO production), or for making an article of manufacture as described herein.

BRIEF DESCRIPTIONS OF THE DRAWINGS

FIG. 1. Mechanism of erythropoietin (EPO) production. Renal interstitial peritubular cells of the kidney detect low blood oxygen levels, and EPO is secreted into the blood. EPO stimulates the proliferation and differentiation of erythroid progenitors into reticulocytes, and prevents apoptosis, causing more reticulocytes to enter the circulating blood. The reticulocytes differentiate into erythrocytes, increasing the erythron size. Oxygen delivery to the tissues is thereby increased.

Figure 2:
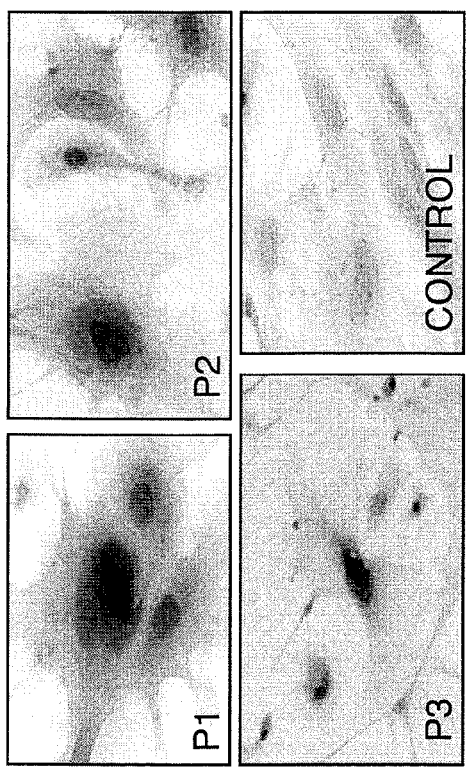

FIG. 2. Intracellular erythropoietin immunoreactivity was confirmed in the primary culture of renal cells at passage 1 (P1), passage 2 (P2) and passage 3 (P3), compared to the negative control (X400).

Figure 3:
Figure 3:
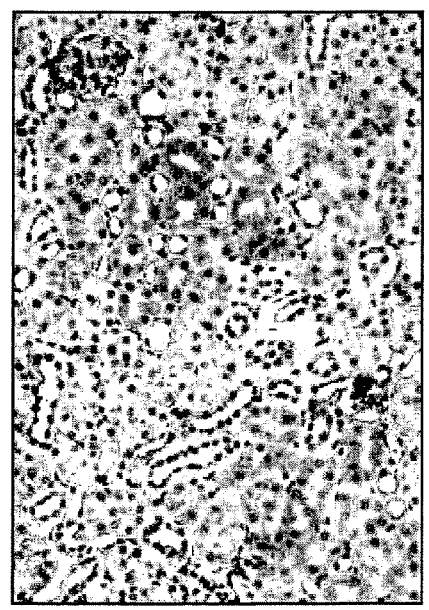

FIG. 3. Microscopy images of erythropoietin expressing cells in kidney tissue (left panel) and in cultured kidney cells (right panel).

Figure 4:
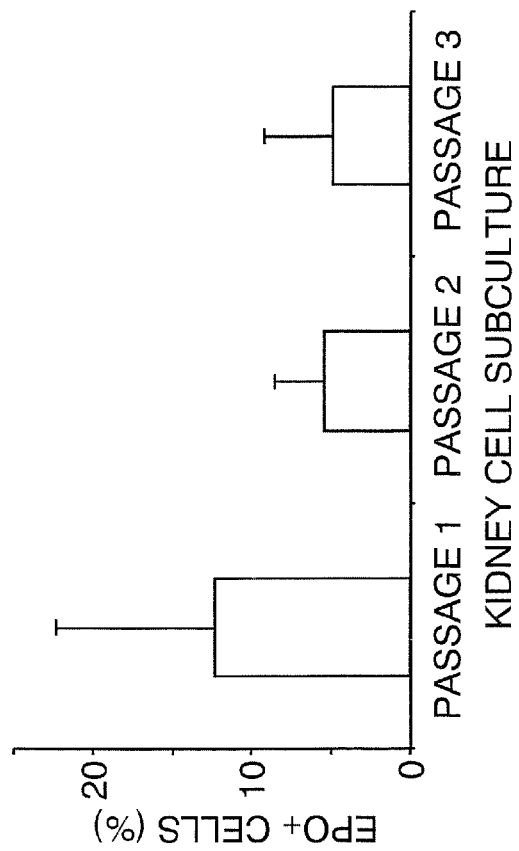

FIG. 4. Quantification of erythropoietin (EPO) producing cells. The number of cells expressing EPO decreased with the subsequent passages (*p<0.05).

Figure 5:
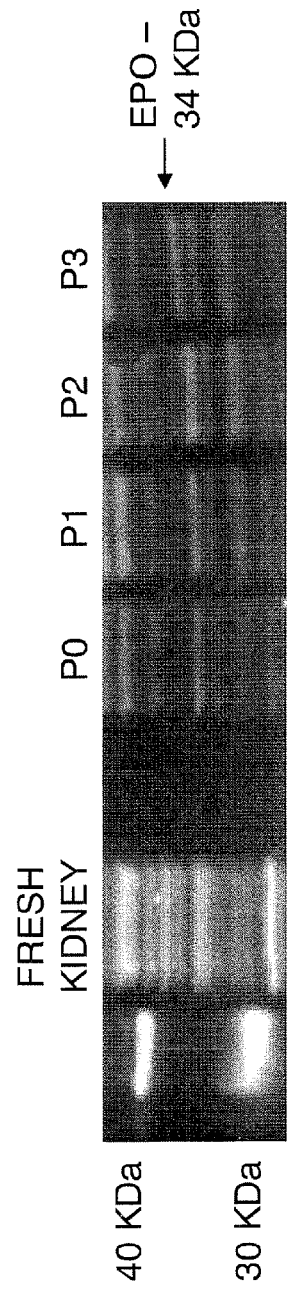

FIG. 5. Western blot analysis of detergent-solubilized cell extracts detected EPO protein (34 kDa) of early passage primary cultured renal cells (P0-P3).

Figure 6:
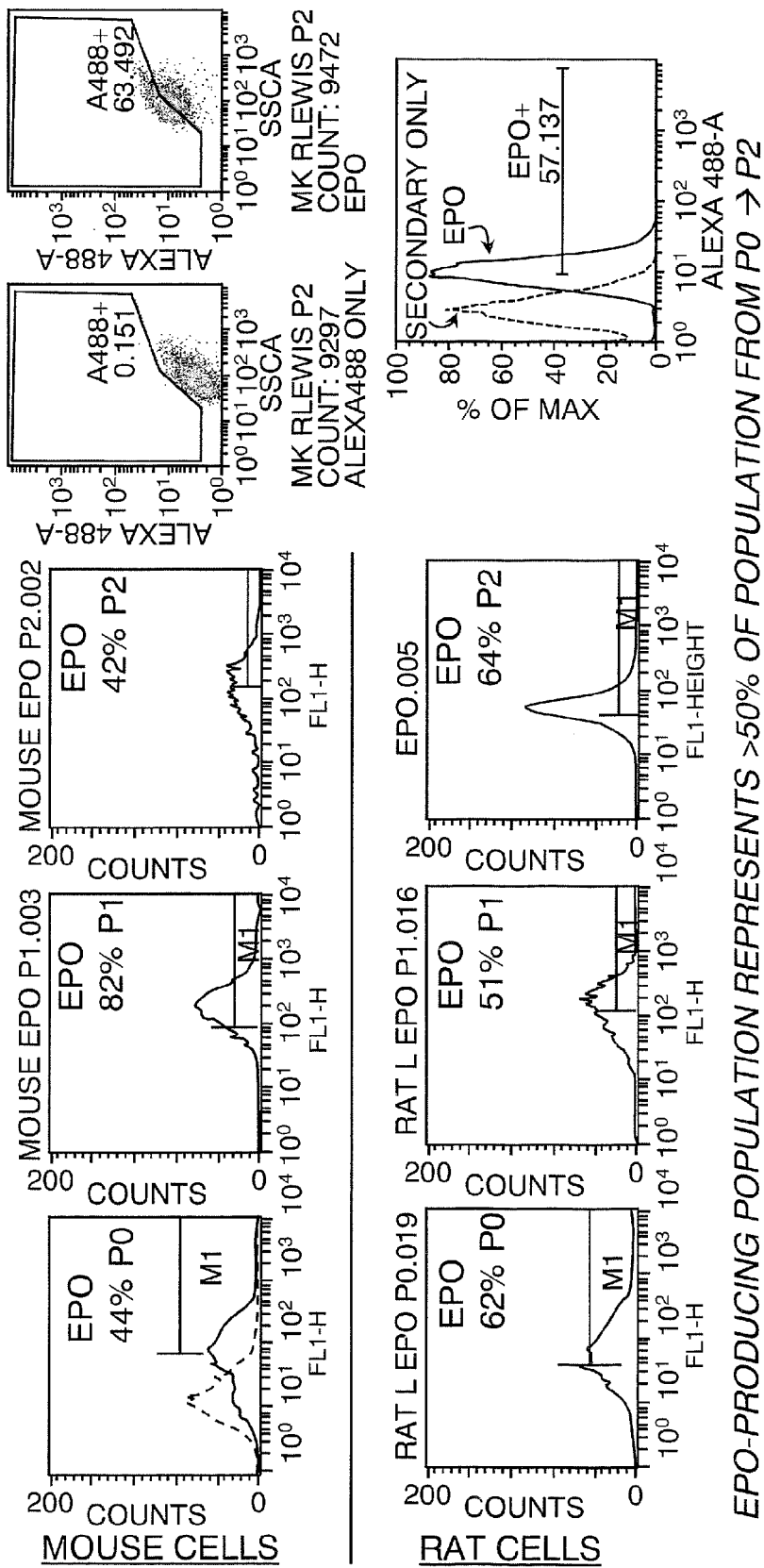

FIG. 6. EPO expression analysis using FACS. Top Row: Mouse cells, passages 0-3. Bottom Row: Rat cells, passages 0-3.

Figure 7A:
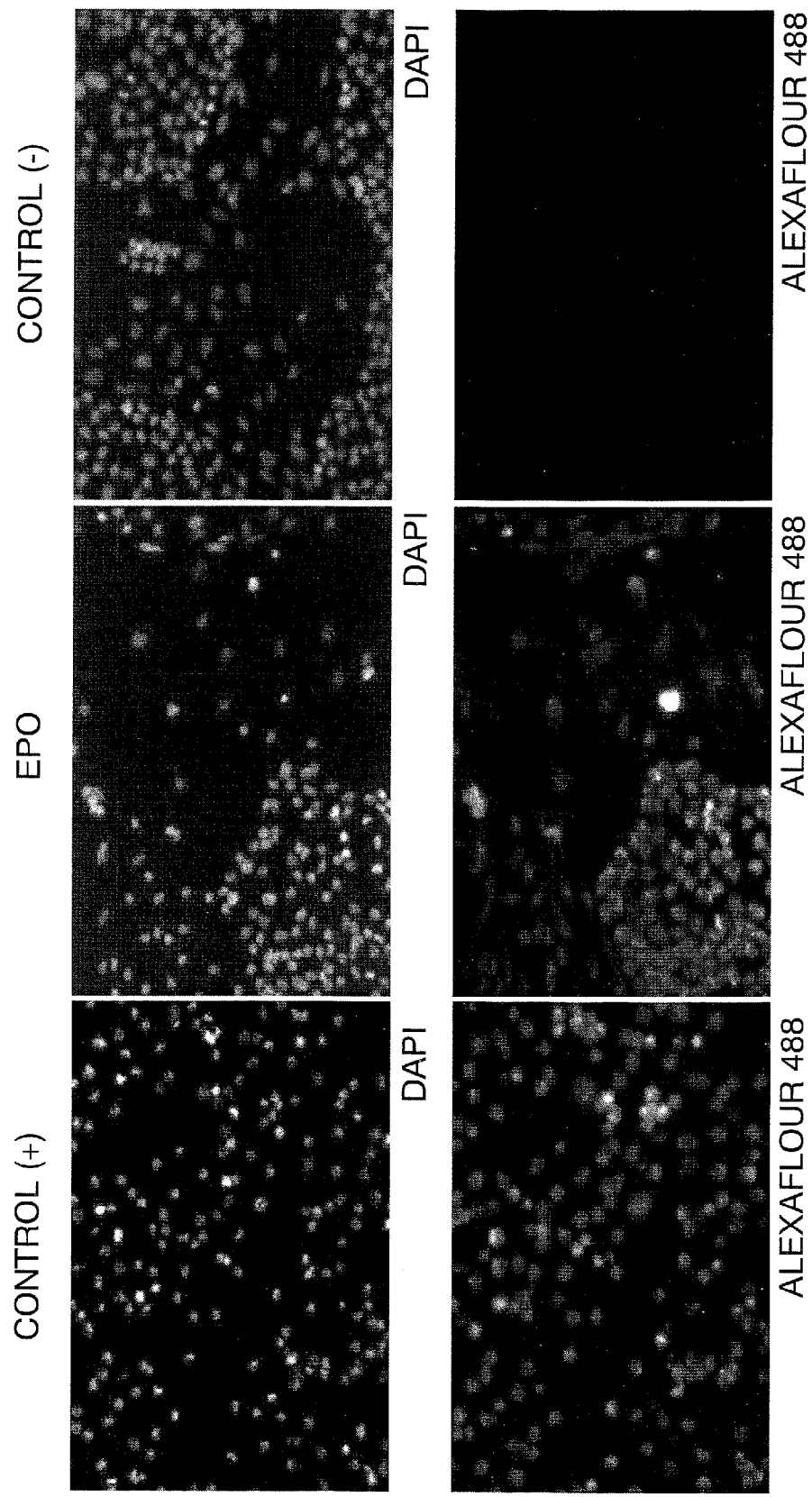
Figure 7B:
Figure 7B:
Figure 7B:
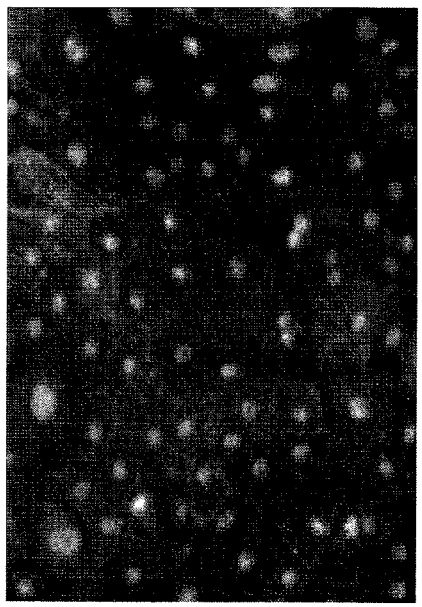
Figure 7B:
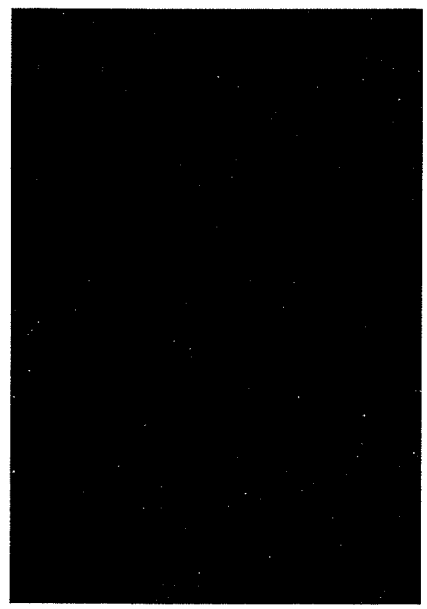

FIG. 7A-7B. Mouse renal cell characterization. EPO expression is confirmed by immunofluorescence (FIG. 7A) (KNRK cells were used as positive control). GLEPP1 and Tamm Horsfall kidney markers were also detected (FIG. 7B).

Figure 8:
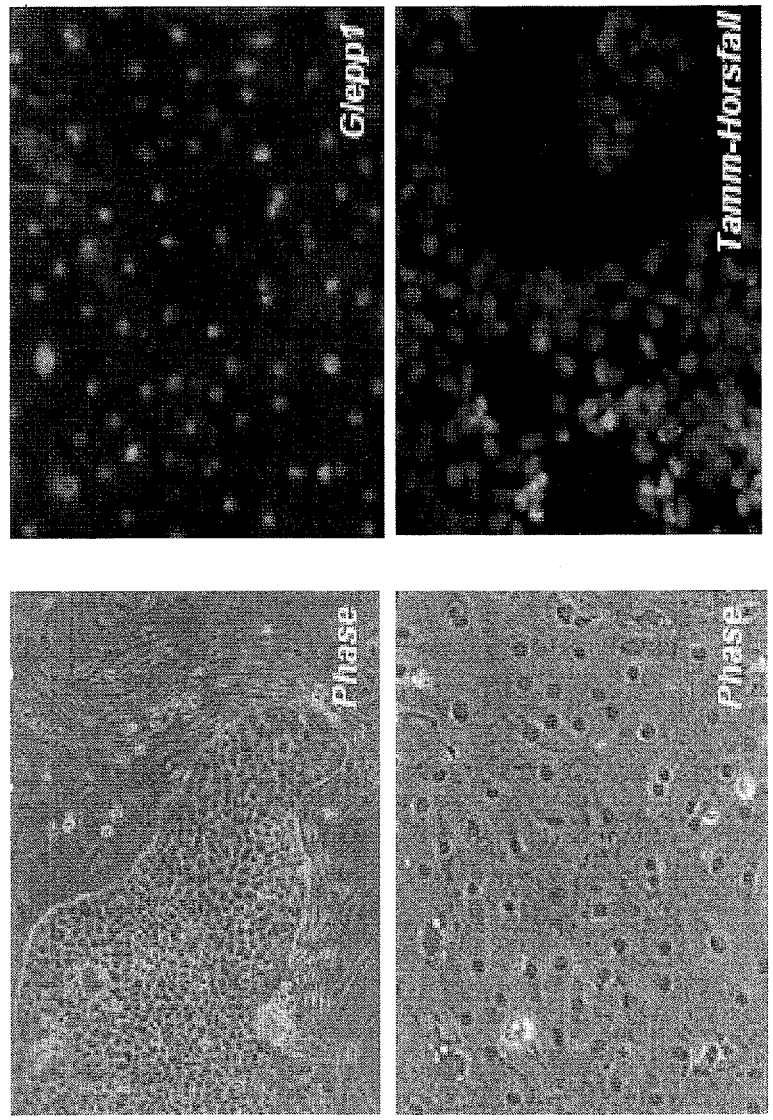

FIG. 8. Rat renal cell characterization. Cultured rat kidney cells have various cell morphologies shown by phase contrast microscope (left panels), and express GLEPP1 and Tamm Horsfall kidney markers (right panels).

Figure 9:
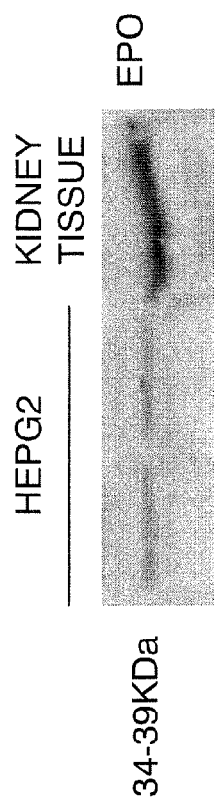

FIG. 9. EPO expression in HepG2 cells was shown by western blot and compared with EPO expression in kidney tissue.

Figure 10:
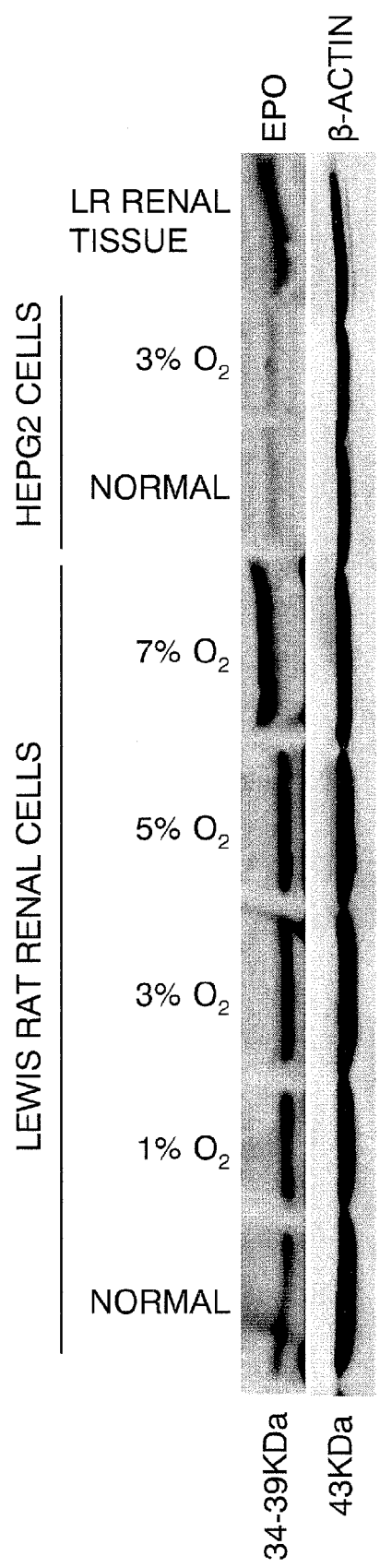

FIG. 10. EPO protein expression of cultured cells under hypoxic conditions. Lewis rat kidney cells and HepG2 cells were cultured under normal and hypoxic conditions, and EPO production was assessed by western blot of cells. 34 kDa=EPO; 43 kDa=β-Actin.

Figure 11:
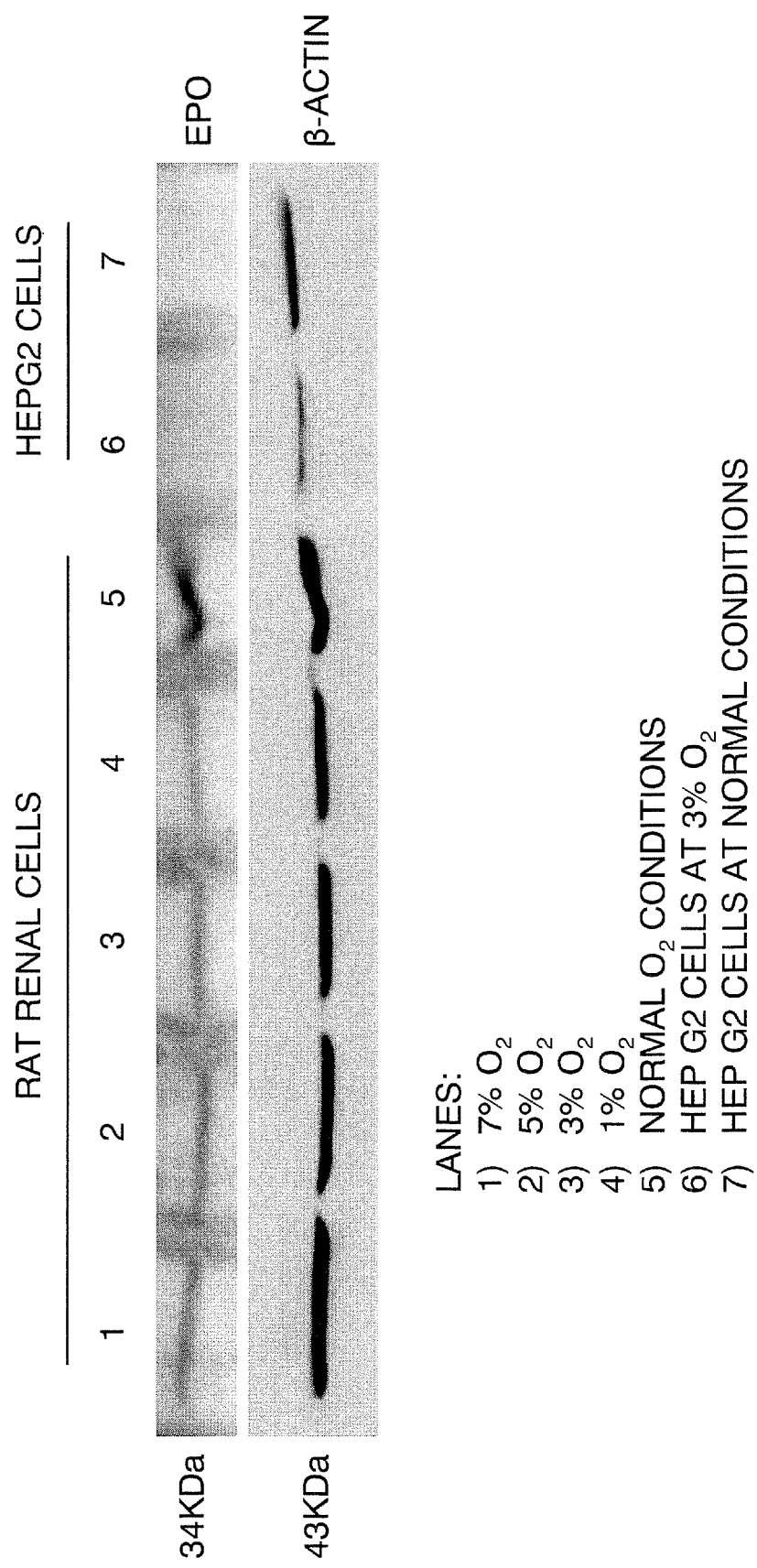

FIG. 11. EPO protein expression in the culture medium under hypoxic conditions. EPO in the culture medium of Lewis rat kidney cells and HepG2 cells was assessed by western blot. 34 kDa=EPO; 43 kDa=β-Actin.

Figure 12:
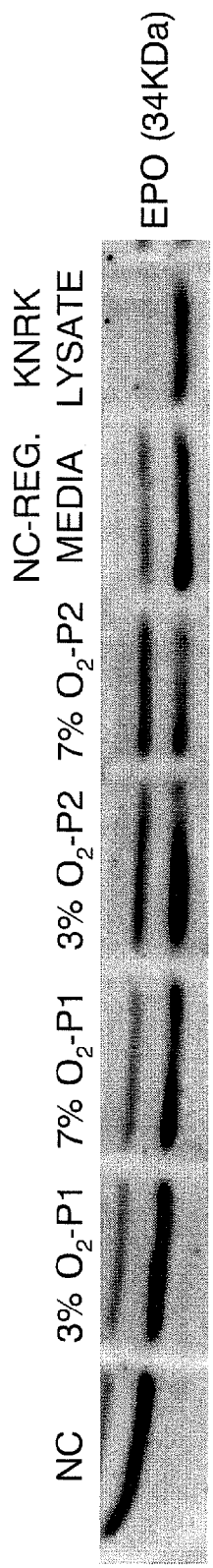

FIG. 12. Total protein lysates were prepared from rat renal primary cells at passages 1 and 2. Plates from normoxic samples (NC), samples in 3% O2 and 7% O2 were processed and run on 10% SDS-PAGE. KNRK cell line was used as positive control.

Figure 13:
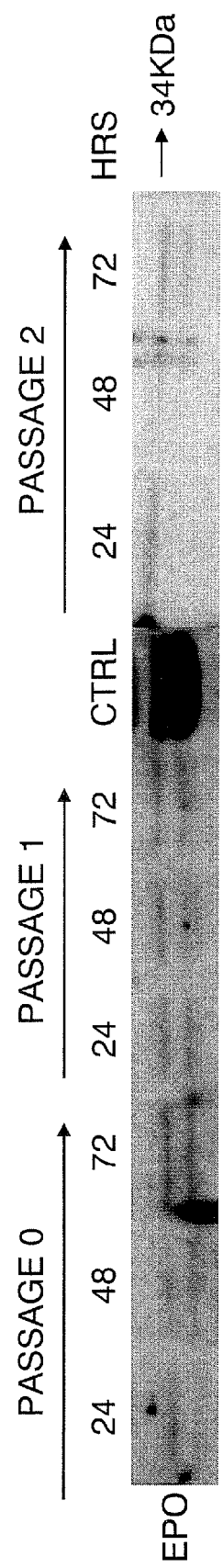

FIG. 13. Measuring EPO in media concentrates by western blot. Primary cultured cells from Lewis rats were raised close to confluency at each passage on 10 cm plates. The cells were starved with KSFM for 24 hrs and then placed in a hypoxic chamber (1% O2) for 24, 48 or 72 hrs. Following hypoxia incubation, the media was collected and concentrated with a 10K mwco amicon ultra centrifugal device (Millipore). 40 ug of total protein was then loaded on a 10% polyacrylamide gel. KNRK cells were used as positive control.

Figure 14:
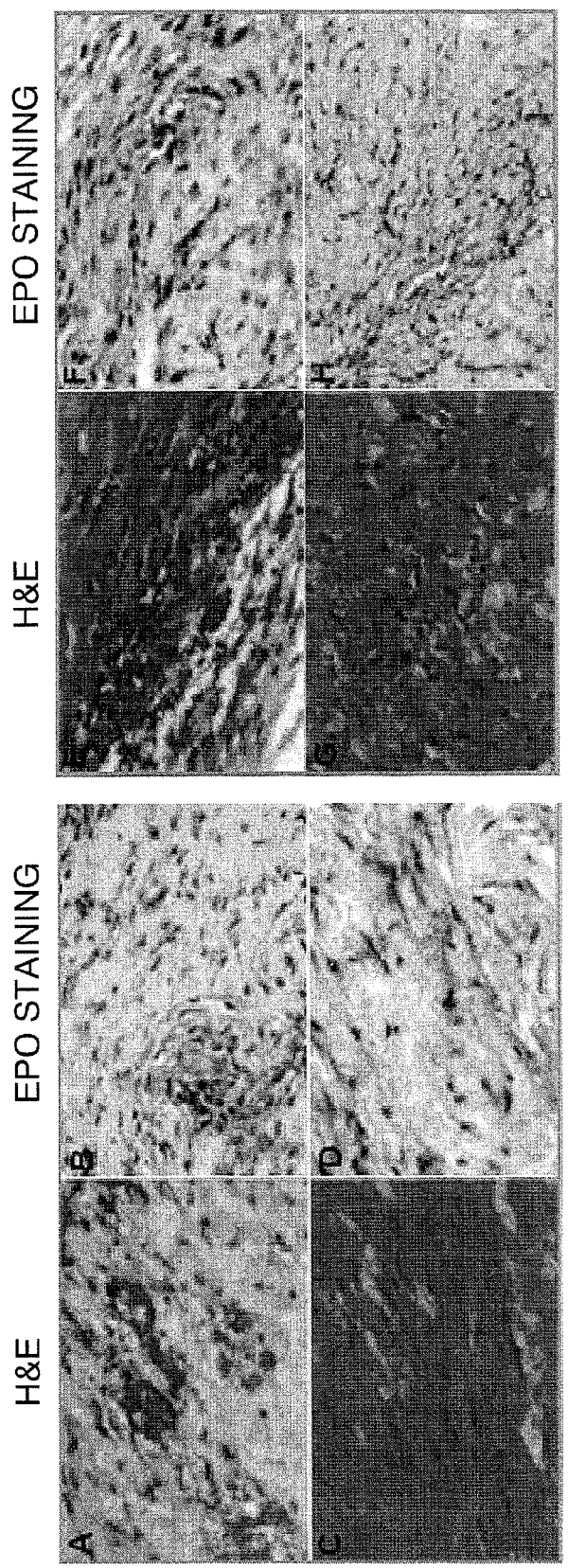

FIG. 14. Histological analysis of the retrieved implants showed that the kidney cells survived and formed tissue in vivo. Presence of EPO producing cells were confirmed immunohistochemically using EPO specific antibodies (X400). Left panel: Initial cell density of $1 \times 10^6$ cells/injection. Right panel: Initial cell density of $1 \times 10^6$ cells/injection. Top row of each panel: 2 weeks. Bottom row of each panel: 4 weeks.

Figure 15:
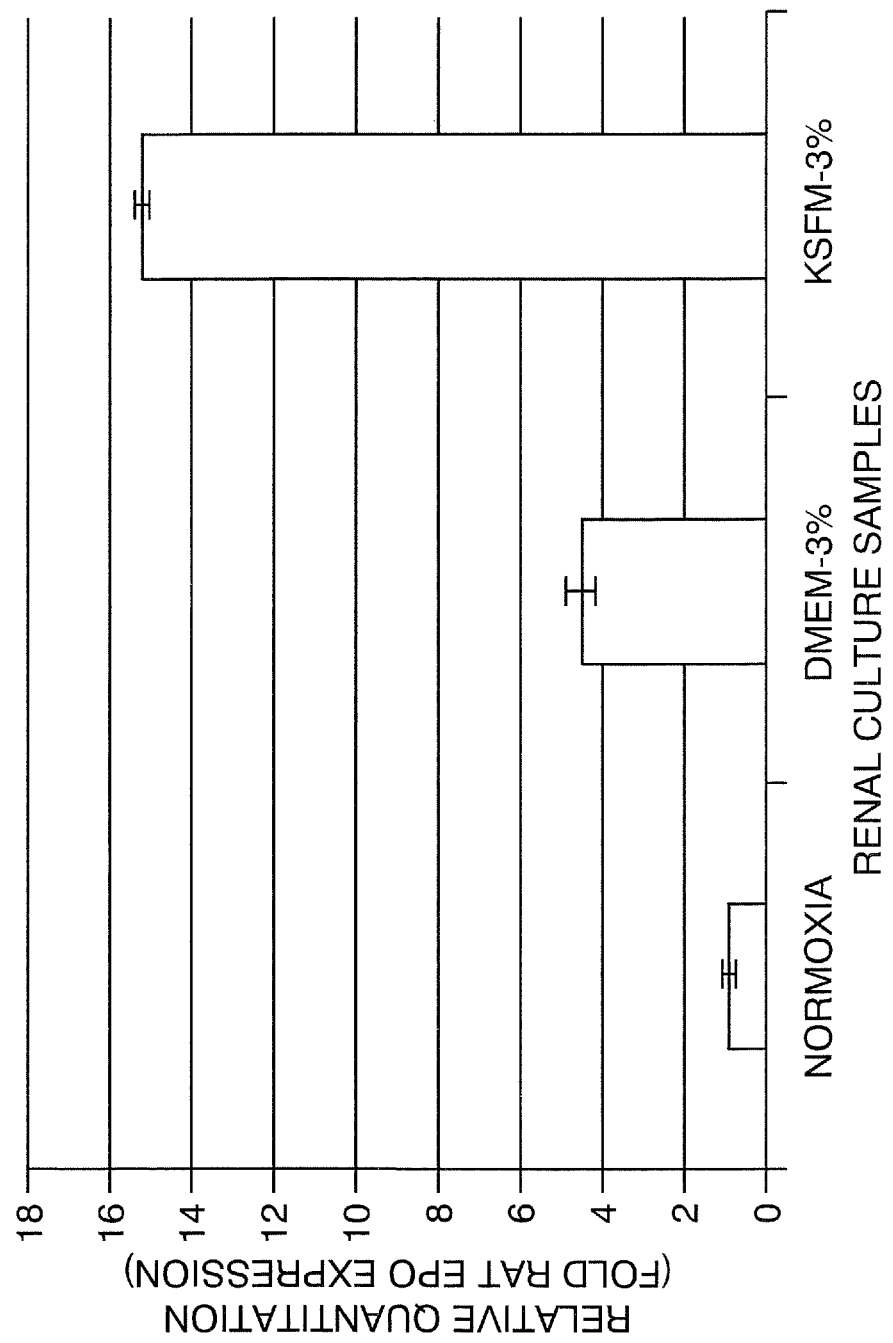

FIG. 15. Effect of culture media and hypoxia on renal primary cells measured by real time PCR. Renal primary cells (p0) were grown to 80% confluency in 10 cm plates. Three plates of cells were grown with either serum free KSFM or DMEM and placed in a hypoxic chamber at 3% O2. After 24 hrs, samples were processed for total RNA and cDNA synthesis. Real time PCR was done in triplicate, and samples were quantified relative to normoxic sample.

Figure 16:
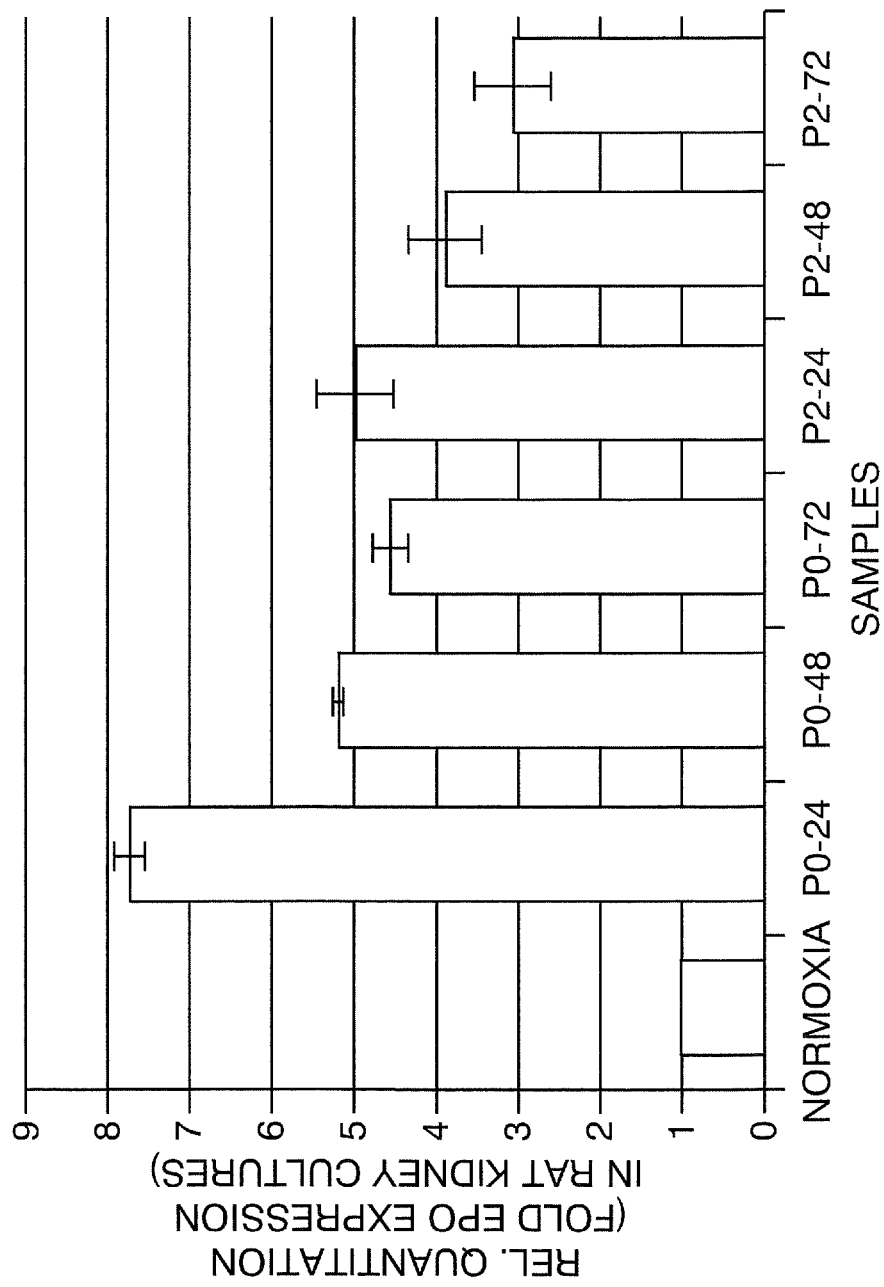

FIG. 16. Effect of hypoxia on renal primary cells measured by real time PCR. Renal primary cells (passages 0 and 2) were grown to 80% confluency in 10 cm plates. Cells were then grown in serum free KSFM and placed in a hypoxic chamber at 1% O2. After 24, 48 or 72 hrs, samples were processed for total RNA and cDNA synthesis. Real time PCR was done in triplicate, and samples were quantified relative to normoxic sample.

Figure 17:
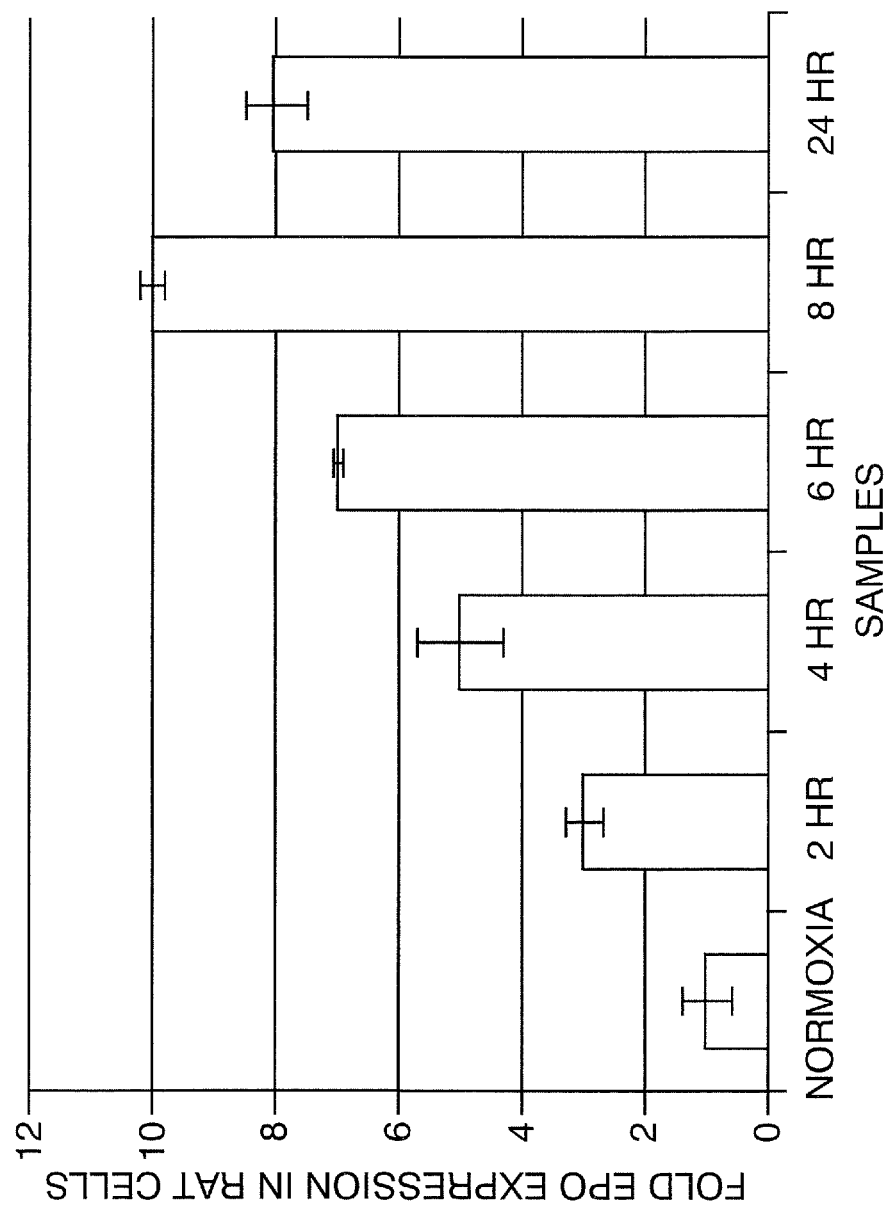

FIG. 17. Effect of hypoxia on renal primary cells measured by real time PCR. Rend primary cells (passage 0) were grown to 80% confluency in 10 cm plates. Cells were then placed in a hypoxic chamber at 1% O2 for up to 24 hrs.

Samples were then processed for total RNA and cDNA synthesis. Real time PCR was done in triplicate, and samples were quantified relative to normoxic sample FIG. 18. Primary human kidney cells were expanded. Shown are cells of passages 2, 4, 7 and 9.

Figure 19:
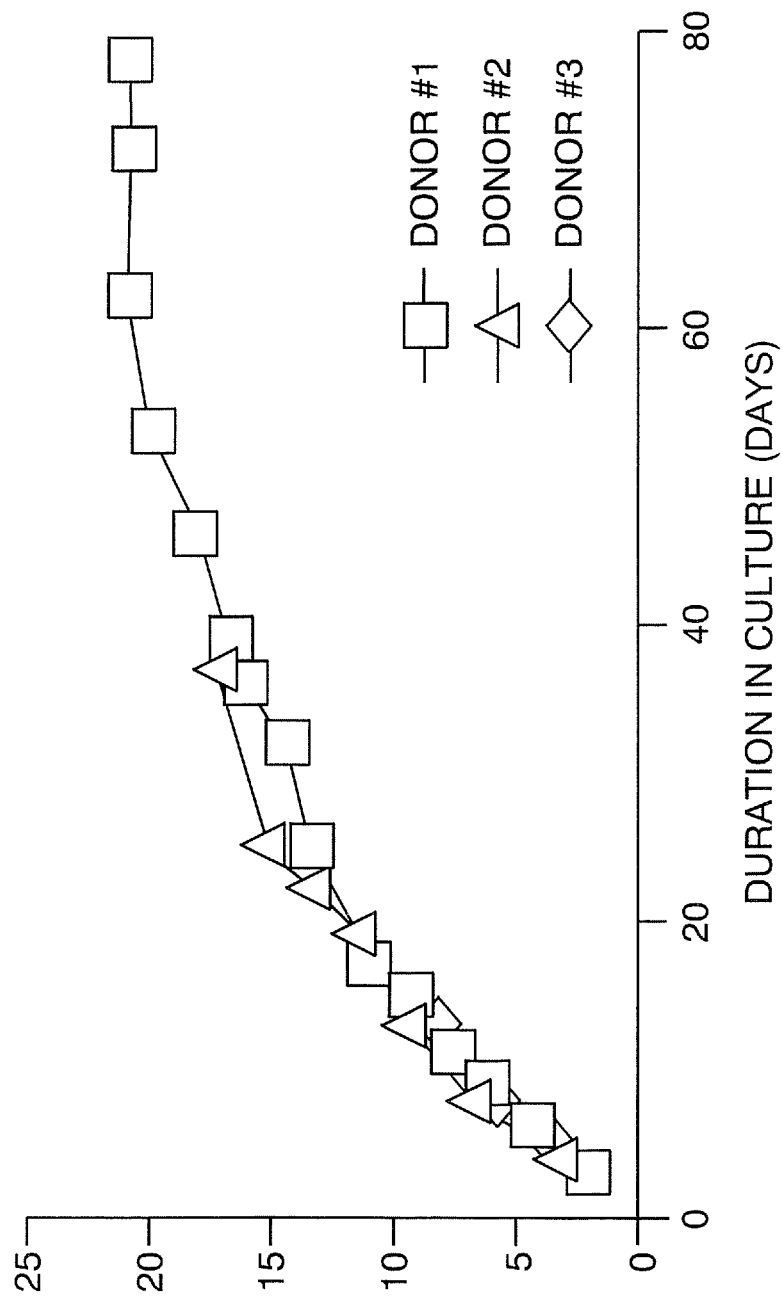

FIG. 19. Human primary renal cells were maintained through 20 doublings.

Figure 20:
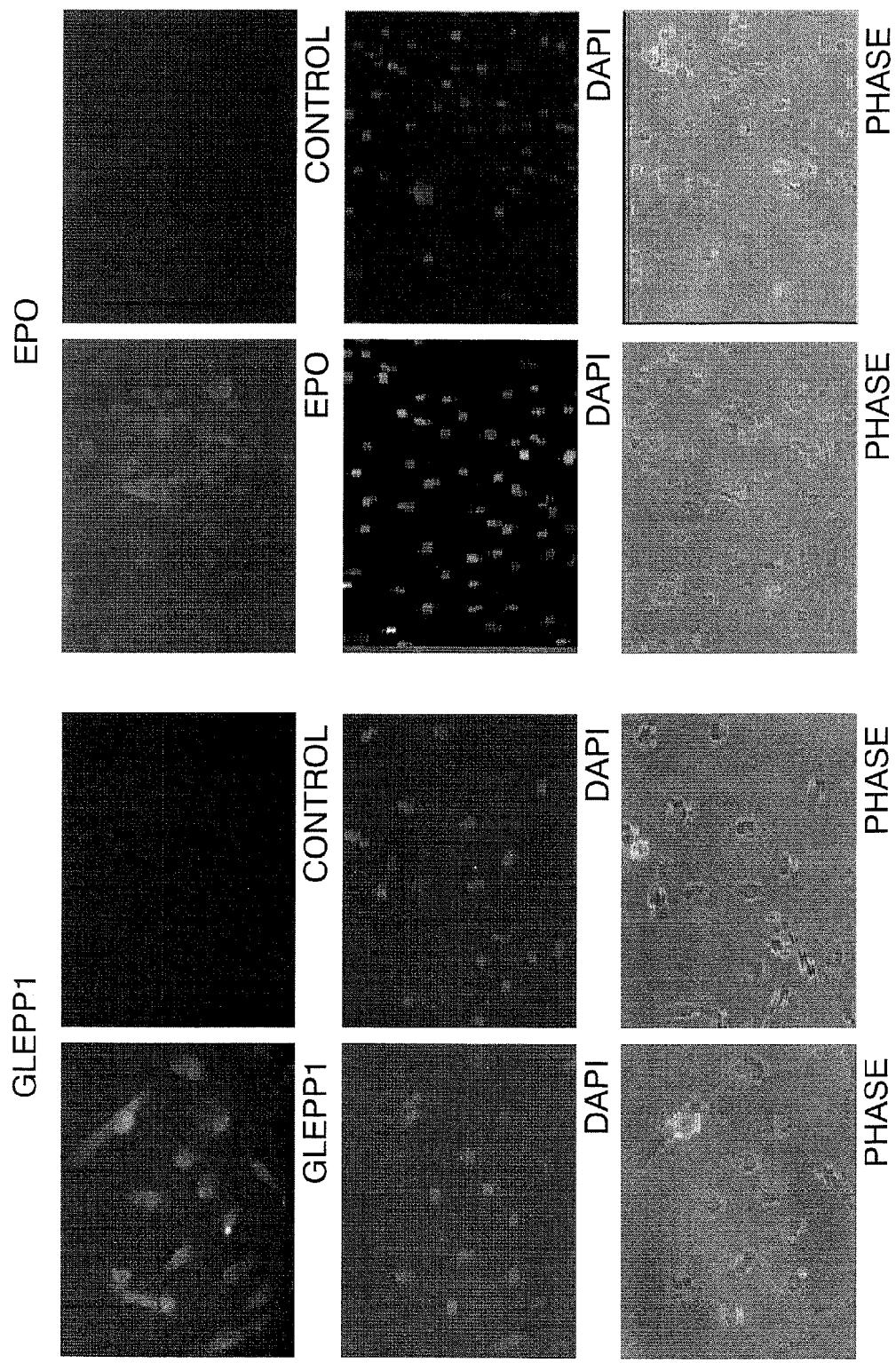

FIG. 20. Human kidney cell characterization. GLEPP1 and EPO positive cells are present in the population.

Figure 21:
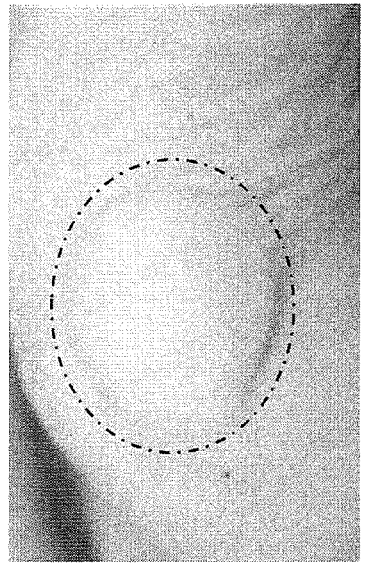
Figure 21:
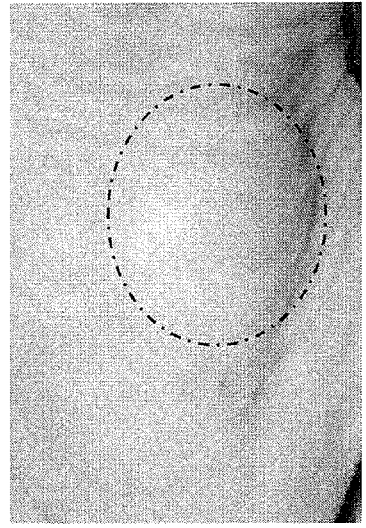

FIG. 21. Human kidney cell delivery in vivo with a 20 mg/ml collagen carrier. At retrieval, 3 weeks after injection, the injection volume had been maintained, and neovascularization was present.

Figure 22:
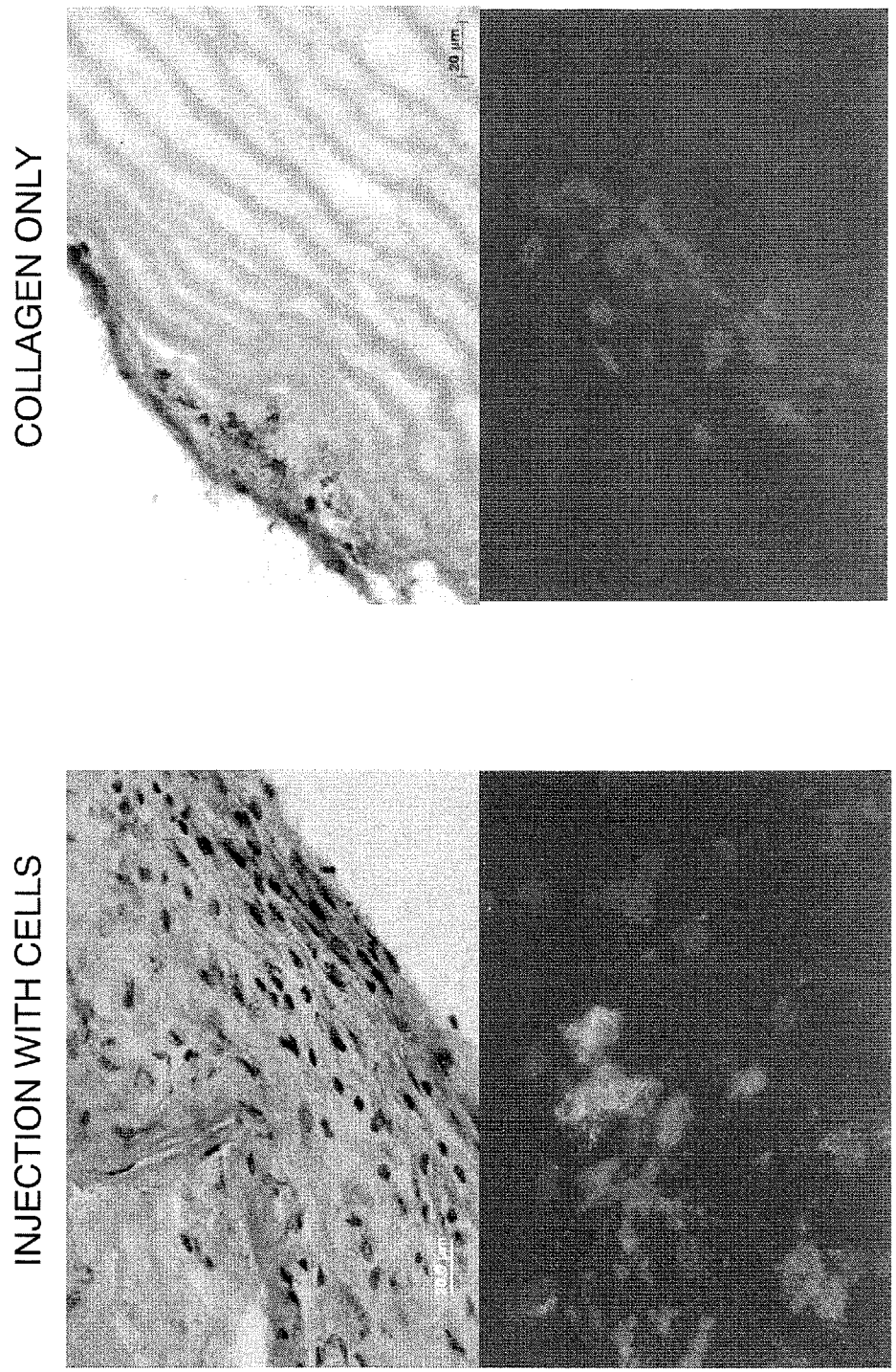

FIG. 22. Injection of collagen with cultured human kidney cells resulted in EPO expressing tissue formation in vivo.

Figure 23:
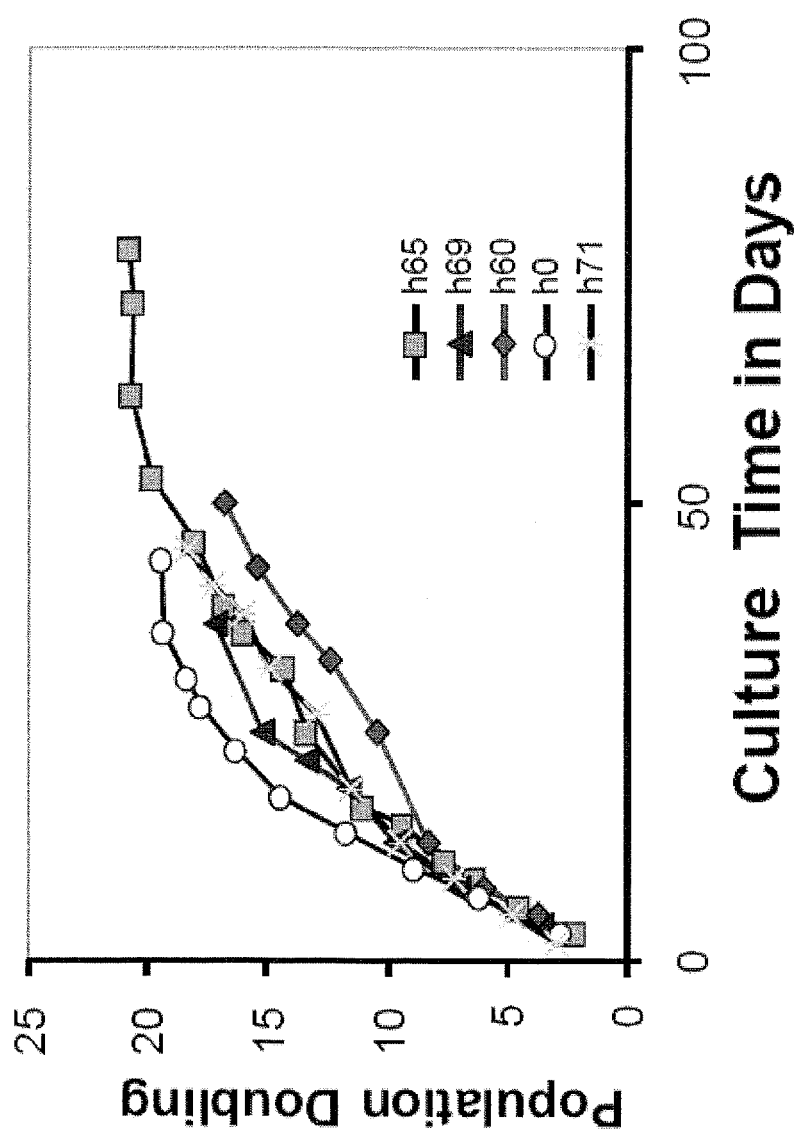

FIG. 23. Human kidney cell growth curve. Human kidney cells obtained from five different donors were cultured and analyzed: h0 human kidney cells from 0-year-old (2 months); h65 human kidney cells from a 65-year-old donor; h71 human kidney cells from 71-year-old donor; and h60 human kidney cells from 60-year-old donor with chronic kidney disease.

Figure 24:
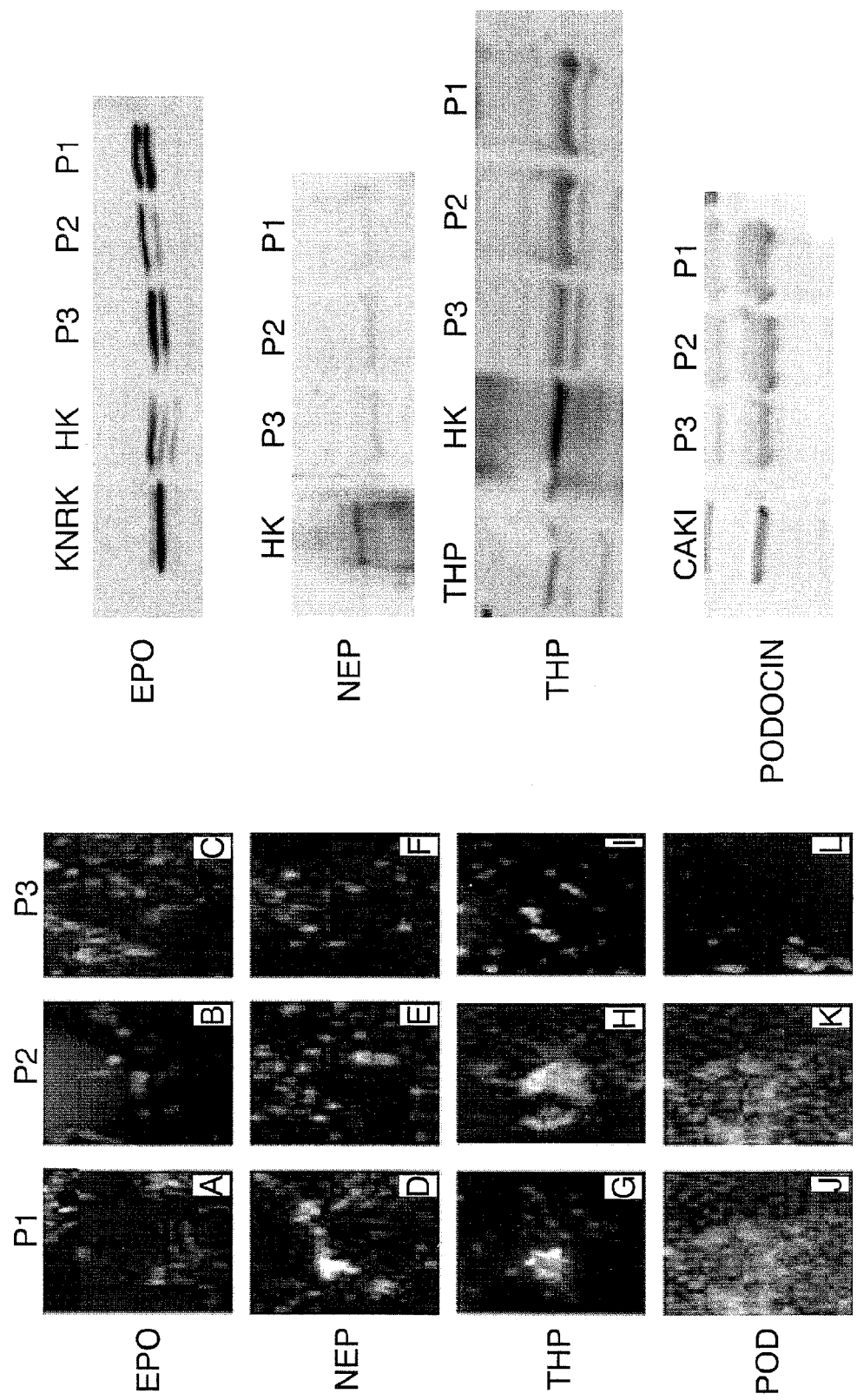

FIG. 24. Human kidney cell characterization. Left: immunocytochemistry of human kidney cells shows the expression of erythropoietin (A-C), neprilysin (D-F), Tamm-Horsfall protein (G-I), and podocin (J-L) in human kidney cells, passages 1, 2 and 3. Right: western blot analysis of human kidney cells confirmed the expression of the cell-specific proteins at passages 1-3.

Figures 25A, 25B:
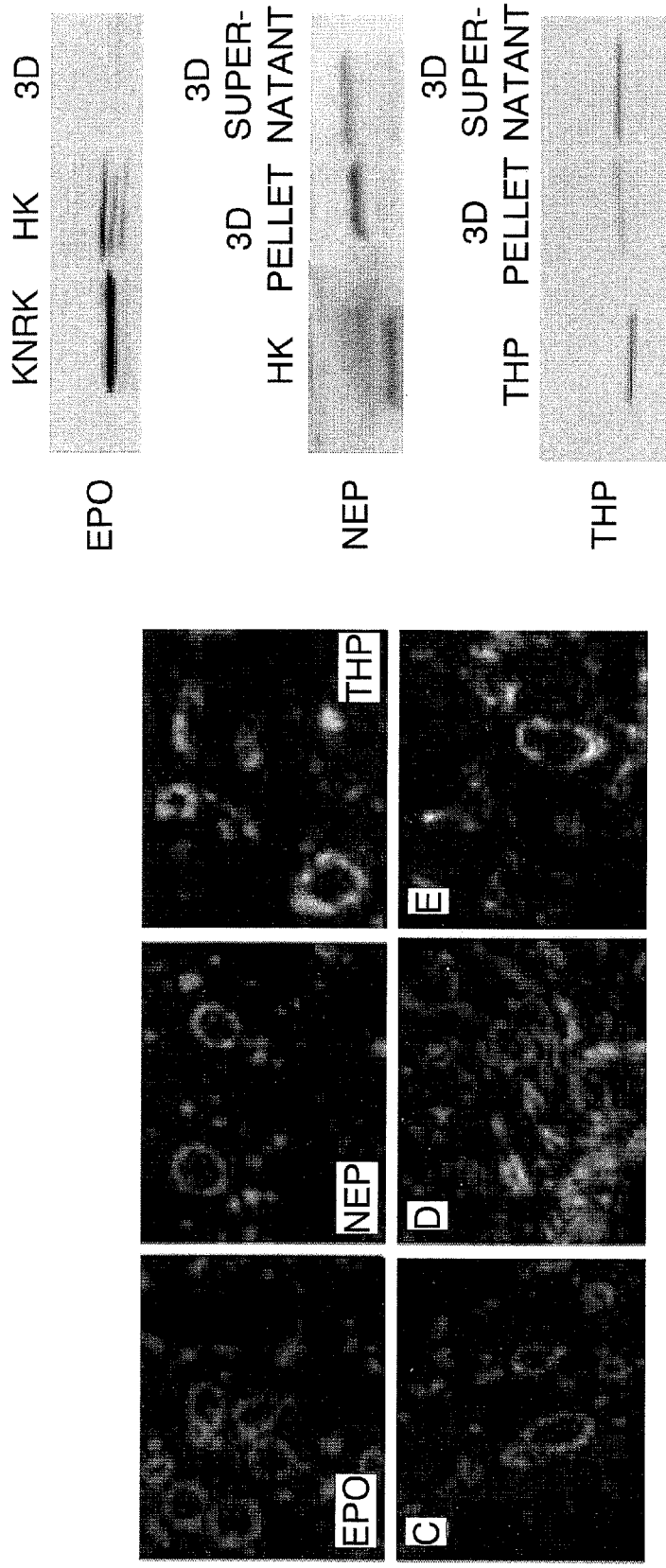

FIG. 25. Formed renal structures were characterized. A: expression of erythropoietin, neprilysin and Tamm-Horsfall protein were expressed in the newly formed structures. B: western blot analysis confirmed the expression using the same proteins in Panel A. C: E-cadherin was expressed in the formed structures. D: E-cadherin in the structures. E: Na—K ATPase expression.

DETAILED DESCRIPTION OF THE PREFERRED EMBODIMENTS

Cell based therapy for renal failure can be approached in two directions: total and selective. Described herein is the selective cell therapy approach for achieving restoration of specific functional organ components.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Kidney tissue" is tissue isolated or harvested from the kidney, which tissue contains kidney cells. In some embodiments, kidney cells are positive for one or more known kidney markers, e.g., GLEPP1, Tamm Horsfall, etc. "Cell" or "cells" may be of any suitable species, and in some embodiments are of the same species as the subject into which tissues produced by the processes herein are implanted. Mammalian cells (including mouse, rat, dog, cat, monkey and human cells) are in some embodiments particularly preferred. "Isolated" as used herein signifies that the cells are placed into conditions other than their natural environment. Tissue or cells are "harvested" when initially isolated from a subject, e.g., a primary explant. Harvesting of kidney tissue may be performed in accordance with methods known in the art. See also U.S. Patent Application Publication No. 2004/0167634 (Atala et al.), which is incorporated by reference herein.

"Subjects" are generally mammalian, including human, subjects and include, but are not limited to, "patients." The subjects may be male or female and human subjects may be of any race or ethnicity, including, but not limited to, Caucasian, African-American, African, Asian, Hispanic, Indian, etc. The subjects may be of any age, including newborn, neonate, infant, child, adolescent, adult, and geriatric.

Subjects and patients may also include animal subjects, particularly mammalian subjects such as canines, felines, bovines, caprines, equines, ovines, porcines, rodents (e.g., rats and mice), lagomorphs, non-human primates, etc., for, e.g., veterinary medicine and/or pharmaceutical drug development purposes.

Cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the patient to be treated) and isogeneic (i.e., a genetically identical but different subject, e.g., from an identical twin). Cells may be obtained from, e.g., a donor (either living or cadaveric) or derived from an established cell strain or cell line. Cells may be harvested from a donor, e.g., using standard biopsy techniques known in the art.

The "primary culture" is the first culture to become established after seeding disaggregated cells or primary explants into a culture vessel. "Expanding" as used herein refers to an increase in number of viable cells. Expanding may be accomplished by, e.g., "growing" the cells through one or more cell cycles, wherein at least a portion of the cells divide to produce additional cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics (e.g., the ability to express EPO).

"Express" or "expression" of EPO means that a gene encoding EPO is transcribed, and preferably, translated. Typically, according to the present invention, expression of an EPO coding region will result in production of the encoded polypeptide, such that the cell is an "EPO producing cell." In some embodiments, cells produce EPO without further manipulation such as the introduction of an exogenous gene. In some embodiments, the invention is subject to the proviso that the EPO producing cells are not manipulated by the introduction of an exogenous gene and/or by an exogenous chemical that stimulates the production of EPO.

In some embodiments, harvested cells are not passaged. In other embodiments, cells are passaged once, twice, or three times. In still other embodiments, cells are passaged more than 3 times. In some embodiments, cells are passaged 0-1, 0-2 or 0-3 times. In some embodiments, cells are passaged 1-2, 1-3, or 1-4 or more times. In some embodiments, cells are passaged 2-3 or 2-4 or more times. In further embodiments, cells are passaged 5, 8, 10, 12 or 15 or more times. In some embodiments, cells are passaged 0, 1, 2, 3 or 4 to 8, 10, 15 or 20 or more times. The number of passages used may be selected by, e.g., the relative EPO production measured in the cell population after each passage.

Growing and expansion of kidney cells is particularly challenging because these cells are prone to the cessation of growth and early differentiation. This challenge is overcome in some embodiments of the present invention by using kidney cell specific media that contains additives that promote their growth. Accordingly, in some embodiments kidney cells are grown in media that includes additives such as growth factors and other supplements that promote their growth. Further, in some embodiments, EPO producing cells are grown in co-culture with other renal cell types.

In some embodiments, kidney cells are grown in Dulbecco's Modified Eagle's Medium (DMEM) supplemented with 10% fetal bovine serum (FBS) or fetal calf serum (FCS) and, optionally, penicillin-streptomycin (P/S). In other embodiments, kidney cells are grown in keratinocyte serum-free medium (KSFM). In further embodiments, kidney cells are grown in KSFM with one or more of the following additives: bovine pituitary extract (BPE) (e.g., 50 g/mL), epidermal growth factor (EGF) (e.g., 5 ng/mL), antibiotic-antimycotic solution (GIBCO) (e.g., 5 mL), fetal bovine serum (FBS) (Gemini Bio-Product) (e.g., 12.5 mL of 2.5%), and insulin transferrin selenium (ITS) (Roche) (e.g., 50 mg for 5 L medium). As understood by those of skill in the art, in some embodiments of the above media, penicillin-streptomycin (P/S) and antibiotic-antimycotic solution are interchangeable.

In some embodiments, kidney cell are grown in media that is a 1:1 mixture of keratinocyte serum-free medium (KSFM) and premixed Dulbecco's Modified Eagle's Medium (DMEM) based media. The premixed DMEM based media according to some embodiments is ¾ DMEM and ¼ HAM's F12 nutrient mixture supplemented with 5% fetal bovine serum (FBS), 1% Penicillin/Streptomycin, 1% glutamine 100×, 1 ml of 0.4 μg/ml hydrocortisone, 0.5 ml of a $10^{-10}$ M cholera toxin solution, 0.5 ml of a 5 mg/ml insulin solution, 12.5 ml/500 ml of a 1.2 mg/ml adenine solution, 0.5 ml of a 2.5 mg/ml transferrin+0.136 mg/ml triiodothyronine mixture, and 0.5 ml of a 10 μg/ml epidermal growth factor (EGF) solution.

Passaging of kidney cells according to some embodiments may be accomplished using standard procedures known in the art. For example, the cells may be detached using trypsin/EDTA and transferred to other plates. This is a standard procedure for many cell types. Briefly, in some embodiments this may be accomplished with the following steps: 1) Remove medium. 2) Add 10 ml PBS/EDTA (0.5 M) for 4 minutes. Confirm the separation of cell junctions under a phase contrast microscope. 3) Remove PBS/EDTA and add 7 ml Trypsin/EDTA. 4) Add 5 ml medium when 80-90% of the cells lift under microscope. 5) Aspirate the cell suspension into a 15 ml test tube. 6) Centrifuge the cells at 1000 rpm for 4 minutes. 7) Remove the supernatant. 8) Resuspend cells in 5 ml of medium. 9) Pipet out 100 μl of the cell suspension and perform trypan blue stain for viability assay. 10) Count the number of cells on hemocytometer. 11) Aliquot the desired number of cells on the plate and make the volume of medium to a total of 10 ml. 12) Place the cells in the incubator.

"Selection" can be based upon any unique properties that distinguish one cell type from another, e.g., density, size, unique markers, unique metabolic pathways, nutritional requirements, protein expression, protein excretion, etc. For example, cells may be selected based on density and size with the use of centrifugal gradients. Unique markers may be selected with fluorescent activated cell sorting (FASC), immunomagnetic bead sorting, magnetic activated cell sorting (MASC), panning, etc. Unique metabolic pathways and nutritional requirements may be exploited by varying the makeup and/or quantity of nutritional ingredients of the medium on which cells are grown, particularly in a serum-free environment. Protein expression and/or excretion may be detected with various assays, e.g., ELISA.

"EPO producing cell" refers to differentiated cells, of which at least a portion produce EPO (e.g., at least 20, 30, 40, or 50% or more, or more preferably 60, 70, 80, or 90% or more of the cells produce EPO). In some embodiments, cells produce EPO without further manipulation such as the introduction of an exogenous gene. In some embodiments, the invention is subject to the proviso that the EPO producing cells are not manipulated by the introduction of an exogenous gene and/or by an exogenous chemical that stimulates the production of EPO. The cells may be harvested from, e.g., the peritubular interstitial cells of the kidney. In some embodiments, the cells are selected for their ability to produce EPO. In other embodiments, the cells are expanded in number by cell culture techniques, e.g., passaging. Cells with the specific function of EPO production can be used from the kidney and from other sources. For example, EPO is also normally produced in the liver.

In the kidney, EPO is generally known to be produced by the interstitial peritubular cells (FIG. 1). In some embodiments, an isolated population of differentiated kidney cells comprises, consists of or consists essentially of interstitial peritubular cells of the kidney, consisting of or consisting essentially of 80, 90, 95, or 99 percent or more, or not more than 20, 10, 5 or 1 percent or less, by number of other cell types. In other embodiments, the isolated population of differentiated kidney cells includes other cell types, e.g., endothelial peritubular cells.

In some embodiments, the isolated population of differentiated kidney cells comprises, consists of or consists essentially of kidney cells that are selected for EPO production, consisting of or consisting essentially of 80, 90, 95, or 99 percent or more, or not more than 20, 10, 5 or 1 percent or less, by number of cells not expressing EPO. Selection may be accomplished by selecting the cells that express EPO using specific markers. In some embodiments, cells may include various types of kidney cells, so long as the cells express EPO. In further embodiments, the entire renal cell colony may be used for expansion and treatment.

In some embodiments, the isolated population of differentiated kidney cells have a "longevity" such that they are capable of growing through at least 5, 10, 15, 20, 25 or 30 or more population doublings when grown in vitro. In some embodiments, the cells are capable of proliferating through 40, 50 or 60 population doublings or more when grown in vitro.

"Differentiated" refers to cells or a population containing cells that have specialized functions, e.g., EPO production and/or expression of known markers of differentiated cells (e.g., GLEPP1 and/or Tamm Horsfall kidney cell markers). In this sense they are not progenitor or stem cells. Some embodiments of the present invention are subject to the proviso that harvested differentiated cells are not passaged under conditions to create a population of less specialized cells.

Alternatively, in other embodiments, cells are cultured to produce cell lines, which may later be differentiated to produce more specialized cells. The establishment of "cell lines," as opposed to cell strains, are by and large undifferentiated, though they may be committed to a particular lineage. Propagation naturally favors the proliferative phenotype, and in some embodiments cells may require a reinduction of differentiation by, e.g., alteration of the culture conditions. There are a number of differentiation factors known in the art that may induce differentiation in cell lines (e.g., cytokines such as epimorphin and HGF, vitamins, etc.).

Renal Cell 3D Culture.

In some embodiments, cells are cultured in a three dimensional (3D) matrix. Such matrix is useful for, inter alia, culturing the cells prior to their administration in methods of treatment, and as an in vitro model system for physiological and developmental studies and/or testing the effects of drugs and/or nephrotoxicity.

"Three dimensional matrix" as used herein refers to a matrix of sufficient length, width and height dimensions to allow cells seeded therein to grow and organize therethrough to form a tissue (an aggregate of cells of a particular kind together with their intercellular substance, forming one of the structural materials found in an animal).

In some embodiments, the matrix material is a polymeric matrix. Examples of suitable polymers include, but are not limited to, collagen, poly(alpha esters) such as poly(lactate acid), poly(glycolic acid), polyorthoesters and polyanhydrides and their copolymers, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyestercarbonate, polyether, polyetheretherketone, polyetherimide, polyetherketone, polyethersulfone, polyethylene, polyfluoroolefin, polylmide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends of these materials.

In some embodiments, the matrix comprises a gel (e.g., a hydrogel) (optionally solidified after seeding). Hydrogel compositions can include, without limitation, for example, poly(esters), poly(hydroxy acids), poly(lactones), poly (amides), poly(ester-amides), poly(amino acids), poly(anhydrides), poly(ortho-esters), poly(carbonates), poly(phosphazines), poly(thioesters), polysaccharides and mixtures thereof. Furthermore, the compositions can also include, for example, a poly(hydroxy) acid including poly(alpha-hydroxy) acids and poly(beta-hydroxy) acids. Such poly(hydroxy) acids include, for example, polylactic acid, polyglycolic acid, polycaproic acid, polybutyric acid, polyvaleric acid, and copolymers and mixtures thereof.

Other embodiments of three dimensional matrix materials may be found in U.S. Patent Application Publication No. 2007/0116679 (Atala), which is incorporated by reference herein.

In some embodiments, the matrix comprises, consists of or consists essentially of collagen. In some embodiments, the matrix comprises, consists of or consists essentially of neutralized Type I collagen. Cells may be seeded onto the matrix and incubated in conditions conducive to their growth in accordance with tissue culture methods described herein and known in the art.

In some embodiments, the matrix has a length, width and height such that one of these dimensions is not substantially smaller than the other two, as opposed to a thin sheet or flat surface. In some embodiments, the three dimensional matrix has a length, width and height that do not differ from one another by more than a factor of 2, 3, 4 or 5.

In some embodiments, the three dimensional culture matrix is created by mixing a collagen type I solution (BD Sciences) and 10× Medium 199 in a 9:1 ratio, respectively. To neutralize the solution, in some embodiments, a base such as NaOH is added until the medium color turns from yellow to red (about 23 µL 1N NaOH for a 1 mL gel solution).

In some embodiments, cells are seeded onto the matrix by mixing the cells and neutralized collagen solution, e.g., in a 5:1, 4:1, 3:1, 2:1, 1:1, 1:2, 1:3, 1:4 or 1:5 ratio, respectively, by volume. In some embodiments, the mixing is performed on ice, or at a temperature between 0 and 20 degrees Celsius. The mixture is then gelled (solidified) by incubation at approximately 37 degrees Celsius (e.g., for 10, 20, 30 or 40 minutes). The mixture may optionally be transferred on to a tissue culture dish prior to gelling. Medium is added to the seeded matrix after solidifying, and changed as needed (e.g., every 2 days).

Methods of Treatment.

In some embodiments, EPO producing cells are administered to a subject in need thereof (e.g., by injection) to the kidney (e.g., into the cortex and/or medulla). In other embodiments, EPO producing cells are administered to other areas of the body, e.g., the liver, peritoneum, etc. In some embodiments, the EPO producing cells are administered subcutaneously, subcapsular, etc. In further embodiments, EPO producing cells are administered by implantation of a substrate (e.g., a collagen gel scaffold) containing said EPO producing cells described herein. In still other embodiments, EPO producing cells are administered through vascular access (e.g., systemically or locally).

Diseases that may be treated with the methods disclosed herein include, but are not limited to, anemias. Anemias include, but are not limited to, those associated with renal failure or end-stage renal disease, anemias caused by chemotherapies or radiation, anemias of chronic disorders, e.g., chronic infections, autoimmune diseases, rheumatoid arthritis, AIDS, malignancies, anemia of prematurity, anemia of hypothyroidism, anemia of malnutrition (e.g., iron deficiency), and anemias associated with blood disorders.

"Treat" refers to any type of treatment that imparts a benefit to a patient, e.g., a patient afflicted with or at risk for developing a disease (e.g., kidney disease, anemia, etc.). Treating includes actions taken and actions refrained from being taken for the purpose of improving the condition of the patient (e.g., the relief of one or more symptoms), delay in the onset or progression of the disease, etc.

Other endocrine systems may benefit from the therapies disclosed herein, for example, vitamin D producing cell therapy or the angiotensin system. See, e.g., U.S. Patent Application Publication No. 2005/0002915 to Atala et al., which is incorporated herein by reference. Cells with a specific function can be used from the kidney and other sources, i.e., cells that would produce target functions. For example, EPO is also normally produced in the liver.

Preferably the cells are mixed with or seeded onto a pharmaceutically acceptable carrier prior to administration. "Pharmaceutically acceptable" means that the compound or composition is suitable for administration to a subject to achieve the treatments described herein, without unduly deleterious side effects in light of the severity of the disease and necessity of the treatment. Such formulations can be prepared using techniques well known in the art. See, e.g., U.S. Patent Application 2003/0180289; Remington: *The*

*Science and Practice of Pharmacy*, Alfonso R. Gennaro, editor, 20th ed. Lippincott Williams & Wilkins: Philadelphia, Pa., 2000. The carrier may be a solid or a liquid, or both (e.g., hydrogels), and can be formulated with the cells as a unit-dose formulation. In some embodiments the cells are provided as a suspension in the carrier to reduce clumping of the cells. In other embodiments cells are seeded onto a biodegradable scaffold or matrix.

In some embodiments, cells are mixed with a suitable gel for administration. Suitable gels that may be used in the present invention include, but are not limited to, agars, collagen, fibrin, hydrogels, etc. Besides gels, other support compounds may also be utilized in the present invention. Extracellular matrix analogs, for example, may be combined with support gels to optimize or functionalize the gel. One or more growth factors may also be introduced into the cell suspensions. See, e.g., U.S. Patent Application Publication No. 2007/0116679 (Atala), which is incorporated by reference herein.

Formulations of the invention include those for parenteral administration (e.g., subcutaneous, intramuscular, intradermal, intravenous, intraarterial, intraperitoneal injection) by injection or implantation. In one embodiment, administration is carried out intravascularly, either by simple injection, or by injection through a catheter positioned in a suitable blood vessel, such as a renal artery. In some embodiments, administration is carried out by "infusion," whereby compositions are introduced into the body through a vein (e.g., the portal vein). In another embodiment, administration is carried out as a graft to an organ or tissue to be augmented as discussed above, e.g., kidney and/or liver.

A "biodegradable scaffold or matrix" is any substance not having toxic or injurious effects on biological function and is capable of being broken down into is elemental components by a host. Preferably, the scaffold or matrix is porous to allow for cell deposition both on and in the pores of the matrix. Such formulations can be prepared by supplying at least one cell population to a biodegradable scaffold to seed the cell population on and/or into the scaffold. The seeded scaffold or matrix may then implanted in the body of a recipient subject.

In some embodiments, cells are administered by injection of the cells (e.g., in a suitable carrier) directly into the tissue of a subject. For example, cells may be injected into the kidney (e.g., the subcapsular space of the kidney). Because the functional effects of EPO production will be systemic, cells may also be administered by injection into other tissues (e.g., the liver, subcutaneously, etc.).

Cells may also be delivered systemically. In further embodiments, cells are delivered to tissue outside of the kidney (e.g., the liver), as the outcome of the functional effects of EPO production will be systemic. See, e.g., the "Edmonton protocol," an established delivery method, where cells are infused into a patient's portal vein (Shapiro et al. (2000) N Engl J Med 343:230-238).

According to some embodiments, the cells administered to the subject may be syngeneic (i.e., genetically identical or closely related, so as to minimize tissue transplant rejection), allogeneic (i.e., from a non-genetically identical member of the same species) or xenogeneic (i.e., from a member of a different species), as above, with respect to the subject being treated, depending upon other steps such as the presence or absence of encapsulation or the administration of immune suppression therapy of the cells. Syngeneic cells include those that are autogeneic (i.e., from the subject to be treated) and isogeneic (i.e., a genetically identical but different subject, e.g., from an identical twin). Cells may be obtained from, e.g., a donor (either living or cadaveric) or derived from an established cell strain or cell line. As an example of a method that can be used to obtain cells from a donor (e.g., a potential recipient of a bioscaffold graft), standard biopsy techniques known in the art may be employed. Alternatively, cells may be harvested from the subject, expanded/selected in vitro, and reintroduced into the same subject (i.e., autogeneic).

In some embodiments, cells are administered in a therapeutically effective amount. The therapeutically effective dosage of cells will vary somewhat from subject to subject, and will depend upon factors such as the age, weight, and condition of the subject and the route of delivery. Such dosages can be determined in accordance with procedures known to those skilled in the art. In general, in some embodiments, a dosage of $1\times10^5$, $1\times10^6$ or $5\times10^6$ up to $1\times10^7$, $1\times10^8$ or $1\times10^9$ cells or more per subject may be given, administered together at a single time or given as several subdivided administrations. In other embodiments, a dosage of between $1-100\times10^8$ cells per kilogram subject body weight can be given, administered together at a single time or given as several subdivided administration. Of course, follow-up administrations may be given if necessary.

Cells may be administered according to some embodiments to achieve a target hematocrit range. The ideal or target hematocrit range may vary from subject to subject, depending upon, e.g., specific comorbidities. In some embodiments the target hematocrit is from 30-40%, in some embodiments the target hematocrit is from 33-38%, and in some embodiments the target hematocrit is from 33-36%. Upon administration of cells according to the present invention, hematocrit may be measured and, if desired or necessary, corrected by, e.g., further implantation of cells and/or other methods known in the art (e.g., supplementing with recombinant EPO). Other methods of treatment for anemia and/or renal disease may be used in conjunction with the methods of treatment provided herein, for example, an adapted protein-caloric intake diet.

In further embodiments, if desired or necessary, the subject may be administered an agent for inhibiting transplant rejection of the administered cells, such as rapamycin, azathioprine, corticosteroids, cyclosporin and/or FK506, in accordance with known techniques. See, e.g., R. Calne, U.S. Pat. Nos. 5,461,058, 5,403,833 and 5,100,899; see also U.S. Pat. Nos. 6,455,518, 6,346,243 and 5,321,043. Some embodiments use a combination of implantation and immunosuppression, which minimizes graft rejection. The implantation may be repeated as needed to create an adequate mass of transplanted tissue.

The present invention is explained in greater detail in the following non-limiting Examples.

EXAMPLES

Anemia is an inevitable outcome of chronic renal failure due to the kidney's decreased ability to produce erythropoietin (EPO) by peritubular interstitial cells. We investigated whether supplementation of erythropoietin producing cells would be a possible treatment option for renal failure-induced anemia by examining the feasibility of selecting and expanding erythropoietin producing cells for cell-based therapy.

The following examples demonstrate that EPO producing cells are present in renal cells harvested from mouse and rat kidneys. In addition, cells isolated and expanded using the methods described below include cells expressing EPO at every culture stage examined. Further, the actual percentage of cells expressing the EPO marker in culture was consistent with the cell population present in normal kidney tissues (see Yamaguchi-Yamada et al., J Vet Med Sci, 67: 891, 2005; Sasaki et al., Biosci Biotechnol Biochem, 64: 1775, 2000; Krantz, Blood, 77: 419, 1991).

Example 1

Expansion of Renal Cell Primary Cultures

Renal cells from 7-10 day old mice C57BL/6 were culture expanded. Minced kidney (1 kidney of mouse) was placed into a 50 cc tube with 15 ml of collagenase/dispase (0.2 mg/ml). The kidney tissue fragments were incubated in a 37° C. shaker for 30 min with collagenase/dispase mix (0.2 mg/ml; 15 ml). Sterile PBS with Gelatin (20 ml), was added (with Gelatin (DIFCO) 2 mg/ml) to the digestion solution. The mixture was filtered thorough a 70 micron filter to remove undigested tissue fragments. The collected solution was mixed well (being careful not to make air bubbles), and divided into two 50 cc tubes. The tubes were centrifuged at 1000(-1500) RPM for 5 min. The supernatant was discarded and the pellet of each tube was resuspended in 3 ml of KSFM medium. DMEM medium (10% FBS, 5 ml P/S) is used for stromal cells, and KSFM with BPE, EGF, 5 ml antibiotic-antimycotic, 12.5 ml FBS (Gemini Bio-Product, 2.5%), Insulin Transferrin Selenium (Roche) (50 mg for 5 L medium) with BPE and EGF for epithelial components. P/S or antibiotic-antimycotic (GIBCO) may also be added. Each tissue was seeded on to a 25 mm plate and medium was added (total 3 ml).

Cells were maintained by changing the medium the next day, and then every 2 days depending on the cell density. Cells were passaged when they were 80-90% confluent by detachment using trypsin/EDTA and transferred to other plates with the following steps: 1) Remove medium. 2) Add 10 ml PBS/EDTA (0.5 M) for 4 minutes. Confirm the separation of cell junctions under a phase contrast microscope. 3) Remove PBS/EDTA and add 7 ml Trypsin/EDTA. 4) Add 5 ml medium when 80-90% of the cells lift under microscope. 5) Aspirate the cell suspension into a 15 ml test tube. 6) Centrifuge the cells at 1000 rpm for 4 minutes. 7) Remove the supernatant. 8) Resuspend cells in 5 ml of medium. 9) Pipet out 100 µl of the cell suspension and perform trypan blue stain for viability assay. 10) Count the number of cells on hemocytometer. 11) Aliquot the desired number of cells on the plate and make the volume of medium to a total of 10 ml. 12) Place the cells in the incubator.

Alternatively, the following protocol was used. Kidneys from 10 day old male C57BL/6 mice were collected in Krebs buffer solution (Sigma Aldrich, St. Louis, Mo. USA) containing 10% antibiotic/antimycotic (Gibco Invitrogen, Carlsbad, Calif. USA) to avoid risk of contamination. The kidneys were immediately transported to a culture hood where the capsule was removed. The medullary region of the kidney was removed, and only the cortical tissue was used to isolate cells that had been previously identified as EPO producing cells (Maxwell et al., Kidney International, 44: 1149, 1993). The kidney tissue was minced and enzymatically digested using Liberase Blendzyme (Roche, Mannheim, Germany) for 25 minutes at 37 degrees Celsius in a shaking water bath. The supernatant was removed and the cell pellet was passed through a 100 µm cell strainer to obtain a single cell suspension for culture.

Subsequently, the cells were plated at a density of $5 \times 10^5$ cells/ml in 10 cm tissue culture treated plates filled with culture media. The culture media consisted of a mixture of keratinocyte serum-free medium (KSFM) and premixed Dulbecco's Modified Eagle's Medium (DMEM) at a ratio of 1:1. The premixed DMEM media contained ¾ DMEM and ¼ HAM's F12 nutrient mixture supplemented with 10% fetal bovine serum (FBS), 1% Penicillin/Streptomycin, 1% glutamine 100x (Gibco), 1 ml of 0.4 µg/ml hydrocortisone, 0.5 ml of a $10^{-10}$ M cholera toxin solution, 0.5 ml of a 5 mg/ml insulin solution, 12.5 ml/500 ml of a 1.2 mg/ml adenine solution, 0.5 ml of a 2.5 mg/ml transferrin+0.136 mg/ml triiodothyronine mixture, and 0.5 ml of a 10 µg/ml epidermal growth factor (EGF) solution. All tissue culture reagents were purchased from Sigma-Aldrich (St. Louis, Mo. USA) unless otherwise stated. The cells were incubated at 37° C. under 5% $CO_2$ with medium change every 3 days, and the cells were subcultured for expansion at a ratio of 1:3 when confluent.

Example 2

Characterization for EPO Production

The cells from early passages (1, 2 and 3) were characterized for EPO expression using immunocytochemistry and western blot analysis with specific antibodies (rabbit polyclonal anti-EPO antibodies, sc-7956, Santa Cruz Technologies, Santa Cruz, Calif.).

Renal cells were plated in 8-well chamber slides at a density of 3000 cells per well. The cells were incubated at 37° C. under 5% $CO_2$ for 24 h to allow attachment. This was followed by fixation with 4% paraformaldehyde for 10 minutes at room temperature. Permeabilization of cell membranes was performed by adding 0.1% Triton-X 100 in PBS for 3 minutes at room temperature. Cells were then incubated in goat serum for 30 minutes at room temperature. After washing, cells were incubated with the primary antibodies for 1 h (1:50) at room temperature. Cells were washed a second time and biotinylated goat polyclonal anti-rabbit antibodies (polyclonal anti rabbit IgG, Vector Laboratories, Inc., Burlingame, Calif.) (1:200) were added, followed by incubation at room temperature for 45 minutes. Chromogenic detection of EPO followed a final washing step and was performed using the Vector ABC kit according to the manufacturer's instructions (Vector Laboratories, Inc., Burlingame, Calif.). Slides without the primary antibodies served as internal negative controls, and normal mouse renal tissue served as the positive control.

Renal cells in culture showed multiple phenotypes under the microscope. The cells reached confluency within 7 to 10 days of plating. Many of the cells observed in the first 3 passages after isolation from the kidney stained positively for EPO, as compared to the negative controls, which showed no background or nonspecific staining (FIG. 2), which indicated that the observed staining was likely due to the presence of EPO in the cultures. The number of cells that stained positively for EPO remained constant throughout the 3 passages studied, even when phenotypic changes were observed in the culture during the same time period. Immunohistochemical staining of kidney tissue indicated a similar amount of EPO expression as that found in cultured cells (FIG. 3).

The number of cells expressing EPO decreased slightly with subsequent passages (FIG. 4). This is most likely due to the increased number of passages and loss of cells/function over time and manipulation. However, the relative percentage appears to remain stable after the first passage.

EPO expression was also confirmed by western blot, shown in FIG. 5.

Example 3

Mouse and Rat Renal Cell Characterization

FACS analysis was used to quantify the number of EPO-producing cells in the established renal cell cultures at each passage (1-3 passages). The cells were collected by trypsinization and centrifugation, resuspended in media, and passed through a 70 µm cell strainer to ensure a single cell suspension. After counting the cells, they were spun down and resuspended in PBS at $5-7.5\times10^5$ cells/tube to remove FBS from the cells. The cells were fixed with 2% formaldehyde for 10 minutes at 4° C. and permeabilized using 100% methanol for 10 minutes at room temperature. Subsequently, the cells were resuspended in 3% goat serum in PBS followed by incubation with the rabbit anti-EPO primary antibody sc-7956 (Santa Cruz Biotechnology, Santa Cruz, Calif.) for 45 minutes on ice. Cells were washed twice with 3% goat serum in PBS prior to incubation with fluorescein isothiocyanate (FITC)-conjugated goat anti-rabbit secondary antibodies for 1 hour. The cells were then washed thoroughly with 3% serum in PBS and transferred to the FACS machine (FACS Calibur E6204, Becton-Dickinson, Franklin Lakes, N.J.).

Fluorescent activated cell sorting experiments demonstrated that 44% of passage 1 (P1) cells were EPO positive. This percentage increased to 82% at passage 2 (P2), and then dropped back to 42% at passage 3 (P3). This may indicate that, during the first few days of culture, proliferation of EPO-producing cells and/or upregulation of EPO gene expression occurs in response to the lower oxygen concentration in the media compared to normal living tissue. These responses could then normalize over the next few days, resulting in numbers of EPO-producing cells that are close to those found in renal tissue (FIG. 6, top row).

The FACS data demonstrate the maintenance of EPO expression over several passages. It should be noted that there was a surge in the number of cells expressing EPO (82%) in the passage 2 culture, which was confirmed by several repeat experiments. Though not wishing to be bound to any particular theory, one possible explanation for this phenomenon could be that EPO expression is an inherent trait of all renal cells that can be turned on and off as needed. In this case, following the abrupt change in survival conditions between the body and the culture plate, the cells may have been driven to express EPO momentarily until stabilization of the culture occurred. Consistent with this, the EPO surge was quickly reversed and passage 3 analyses showed a lower percentage of EPO producing cells (42%).

Mouse cell characterization by immunofluorescence confirmed EPO expression (FIG. 7A). The population of cells was positive for the kidney cell markers GLEPP1 and Tamm Horsfall (FIG. 7B).

Rat cell passages 0, 1 and 2 were also analyzed for EPO production using fluorescence activated cell sorting (FACS) (FIG. 6, bottom row). Cultured rat cells had various cell morphologies and were positive for GLEPP1 and Tamm Horsfall kidney cell markers (FIG. 8).

Example 4

Exposure of EPO Producing Cultures to Hypoxic Conditions

While maintenance of phenotypic characteristics is essential during cell expansion stages, a critical component that ensures the success of cell therapy is the ability of EPO producing cells to regulate and maintain normal EPO levels. EPO belongs to the hematopoietic cytokine family, and it controls erythropoiesis in bone marrow, and regulates the proliferation, differentiation and survival of erythroid progenitor cells through EPO receptor (EPOR)-mediated signal transduction. EPO is largely produced in the kidney, and when this organ fails, EPO production falls, leading to anemia. EPO expression in the body depends largely on the oxygen tension in the environment surrounding the cells capable of producing EPO. Factors influencing oxygen levels include lack of oxygen in the ambient air and decreased renal blood flow.

To determine whether the EPO expressing cells in culture could respond to changing oxygen levels, an experiment was performed in which the cells were serum-starved for 24 hours followed by exposing them to various levels of oxygen in vitro. Lewis rat kidney cells and HepG2 (human hepatocellular liver carcinoma cell line) cells were cultured under normal and hypoxic conditions, and EPO production was assessed and confirmed by western blot of cells. EPO presence in the culture medium was also measured and confirmed by analyzing the supernatants from cultured renal cells under normoxic and hypoxic conditions with the double antibody sandwich enzyme-linked immunosorberbent assay using a Quantikine® IVD® Erythropoietin ELISA kit (R&D Systems®, Minneapolis, Minn.).

The cells were placed in serum free media for 24 hours prior to the experiment. The plates were then transferred to a hypoxic chamber and exposed to different hypoxic conditions (1%, 3%, 5%, and 7% oxygen). HepG2 cells were used as positive controls, as they have been previously reported to produce high levels of EPO in culture (Horiguchi et al., Blood, 96: 3743). EPO expression by HepG2 was confirmed by western blot (FIG. 9). All cells were harvested in lysis buffer containing NP-40. Protein concentration in each sample was measured using a Bio-Rad protein assay. 40 µg total protein was run out on a 10% acrylamide gel using SDS-PAGE. Proteins were then transferred onto a PVDF membrane (Millipore Corp.). Detection of β-actin expression in the lysates was used as the loading control. EPO antibody (rabbit polyclonal sc-7956, Santa Cruz Biotechnology) was used at 1:200 and the secondary antibody (goat anti-rabbit 7074, Cell Signaling Technology, Beverly, Mass.) was used at 1:2000. To measure the amount of EPO secreted into the media by the primary renal cultures, the media was collected and concentrated down to 500 ul using an Amicon Ultra centrifugal filter device (Millipore Corporation, Billerica, Mass.). Samples of this media were run on a 10% polyacrylamide gel. EPO antibody (rabbit polyclonal sc-7956, Santa Cruz Biotechnology) was used at 1:100 and the secondary antibody (goat anti-rabbit 7074, Cell Signaling Technology, Beverly, Mass., USA) was used at 1:2000.

Western blotting showed a slight increase in the EPO expression in the cell lysate after hypoxia (FIG. 10). These results, however, were not seen when media concentrates were used to measure EPO (FIG. 11). The media testing indicated that all media concentrates (hypoxic and normoxic conditions) contained the same low amount of EPO.

Alternatively, total protein lysates were prepared from rat renal primary cells at passages 1 and 2. Plates from normoxic samples (NC), samples in 3% O2 and 7% O2 were processed and Run on 10% SDS-PAGE. The KNRK cell line was used as positive control. Results are shown in FIG. 12.

Without wishing to be bound by any particular theory, this may indicate that 24 hours might not be enough time for secreted EPO levels to rise to a level that is detectable by western blot. It is likely that a longer exposure time would be required for the cells to begin to secrete EPO, as de novo protein production may take several hours to become apparent. Therefore the following experiment was performed, in which cells were placed in hypoxic conditions for 24, 48 and 72 hours.

Primary cultured cells from Lewis rats were raised close to confluency at each passage on 10 cm plates. The cells were placed in a hypoxic chamber (1% $O_2$) for 24, 48 or 72 hrs. Following hypoxia incubation, the media was collected and concentrated with a 10K molecular weight cutoff Amicon Ultra centrifugal device (Millipore). 40 μg of total protein was then loaded on a 10% Polyacrylamide gel. KNRK cells were used as a positive control. Results are shown in FIG. 13.

In summary, all experiments indicated that the EPO levels in primary culture cells were greater than or equal to those measured in the HepG2 positive controls, and the EPO producing cells are able to respond to changing environment.

Example 5

Administration of EPO Producing Cells In Vivo

To determine whether EPO producing cells survive and form the tissues in vivo, renal cells mixed in collagen gel were implanted subcutaneously in athymic mice at concentrations of $1 \times 10^6$ and $5 \times 10^6$ followed by retrieval at 14 and 28 days after implantation for analysis. Cells at different passages from 1-5 were used. The cells were suspended in a collagen gel for easy injection (concentration: 0.1 mg/ml).

Histologically, the retrieved implants showed that surviving renal cells continue expressing EPO proteins, confirmed immunohistochemically using EPO specific antibodies (FIG. 14).

These results demonstrate that EPO producing renal cells grown and expanded in culture stably expressed EPO in vivo. Thus, EPO producing cells may be used as a treatment option for anemia caused by chronic renal failure.

Example 6

Analysis of EPO Expression with Real Time PCR

Real time PCR was performed to assess rat cell expression of EPO in response to hypoxic conditions.

To test the effect of culture media, cells grown in either KSFM and DMEM were exposed to hypoxic conditions (3% $O_2$). Renal primary cells (passage 0) were grown to 80% confluency in 10 cm plates. Three plates of cells were grown with either serum free KSFM or DMEM and placed in a hypoxic chamber at 3% $O_2$. After 24 hrs, samples were processed for total RNA and cDNA synthesis. Real time PCR was done in triplicate, and samples were quantified relative to normoxic sample. Results are shown in FIG. 15.

Rat kidney culture EPO expression was compared with real time PCR across 24, 48 and 72 hours. Renal primary cells (passages 0 and 2) were grown to 80% confluency in 10 cm plates. Cells were then grown in serum free KSFM and placed in a hypoxic chamber at 1% O2. After 24, 48 or 72 hours, samples were processed for total RNA and cDNA synthesis. Real time PCR was done in triplicate, and samples were quantified relative to normoxic sample. Results are shown in FIG. 16.

Testing timepoints for up to 24 hours, renal primary cells (passage 0) were grown to 80% confluency in 10 cm plates. Cells were then placed in a hypoxic chamber at 1% O2 for up to 24 hours. Samples were then processed for total RNA and cDNA synthesis. Real time PCR was run in triplicate, and samples were quantified relative to normoxic sample. Results are shown in FIG. 17.

Example 7

Expansion of Human Kidney Cells

Figure 18:
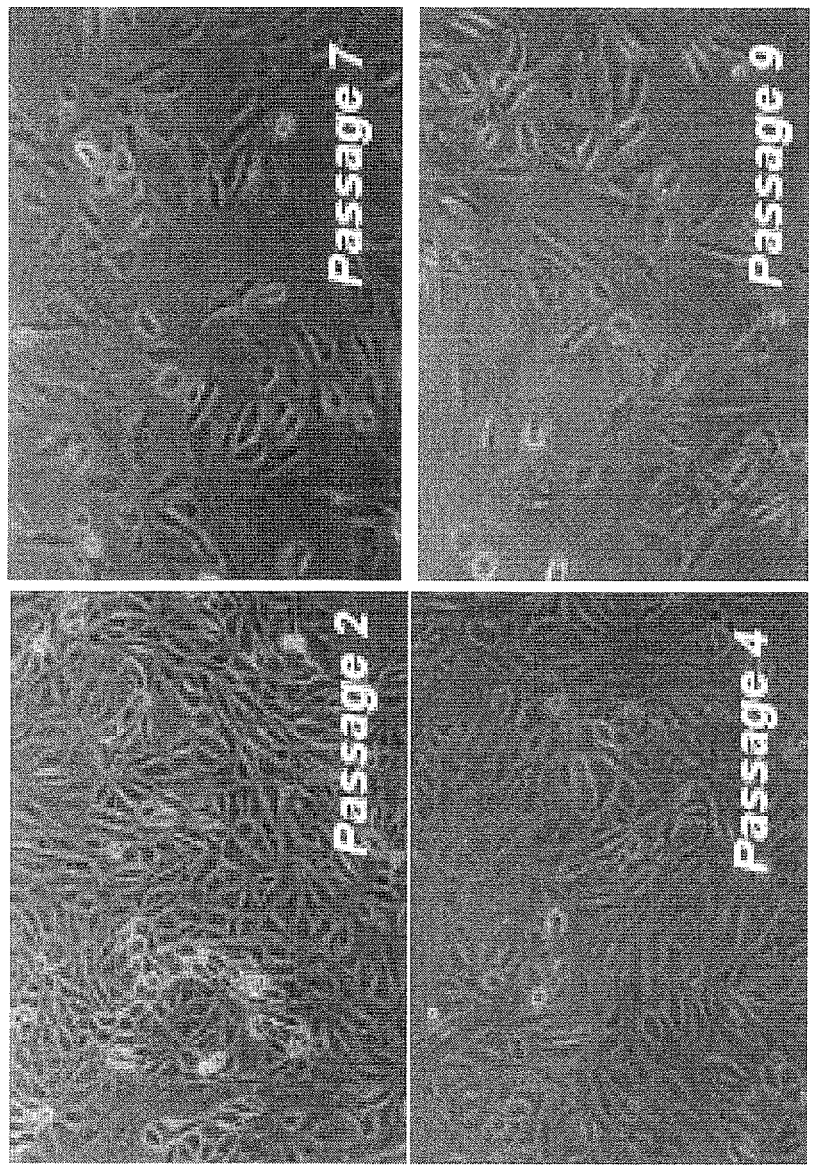

The growth and expandability of primary human kidney cells were also demonstrated using the media and conditions described above. Cultures from passages 2, 4, 7 and 9 are shown in FIG. 18. It was demonstrated that human primary renal cells can be maintained through twenty doublings (FIG. 19). Human kidney cell cultures were characterized for EPO and GLEPP1 expression (FIG. 20).

Example 8

Human Kidney Cell Delivery Via Collagen Injection

Human renal cells mixed in collagen gel were implanted subcutaneously in athymic mice as described above in Example 5. Collagen concentrations of 1 mg/ml, 2 mg/ml and 20 mg/ml were compared. At 1 and 2 mg/ml, the in vivo volume disappeared after administration. At 20 mg/ml, the in vivo injection volume was maintained, and neo-vascularization was seen FIG. 21. Histology confirmed that EPO expressing tissue was formed in vivo (FIG. 22).

Example 9

EPO Producing Cell Selection with Magnetic Cell Sorting

Cells are selected for EPO production using magnetic cell sorting. A single-cell suspension is isolated using a standard preparation method. After preparation of single-cell suspension, count the total number of the cells and centrifuge cell samples to obtain a pellet. Block the cells with 10% of goat serum (of animal where the secondary antibody is made) for 10 minutes. Add 1 or 2 mL of the blocking solution. After 10 minutes of centrifugation, resuspend the cells in the primary antibody for EPO (use 1 μg of the primary antibody/ million of cells). Typically, label for 15 minutes at 4-8° C. is sufficient. Wash the cells twice to remove any unbound primary antibody with 1-2 mL of buffer per $10^7$ cells and centrifuge at 300×g for 10 minutes. After two successive washes, the pellet is resuspended in 80 μL of PBS (0.5% of BSA and 2 mM of EDTA, pH 7.2) per $10^7$ cells. Add 20 μL of Goat Anti-Rabbit MicroBeads per $10^7$ cells. Mix well and incubate for 15 minutes at 4-8° C. Wash the cells twice by adding 1-2 mL of buffer per $10^7$ cells and centrifuge at 300×g for 10 minutes. Pipette off supernatant completely. Resuspend up to $10^8$ cells in 500 μL of buffer (Note: For higher cell numbers, scale up buffer volume accordingly; for depletion with LD Columns, resuspend cell pellet in 500 μL of buffer for up to 1.25×108 cells). Proceed to magnetic cell separation Note: Work fast, keep cells cold, and use pre-cooled solutions. This will prevent capping of antibodies on the cell surface and non-specific cell labeling. Volumes for magnetic labeling given below are for up to $10^7$ total cells. When working with fewer than $10^7$ cells, use the same volumes as indicated. When working with higher cell numbers, scale up all reagent volumes and total volumes accordingly (e.g. for $2\times10^7$ total cells, use twice the volume of all indicated reagent volumes and total volumes). Working on ice may require increased incubation times. Higher temperatures and/or longer incubation times lead to non-specific cell labeling.

Example 10

In Vitro Reconstitution of Human Kidney Structures for Renal Failure

End stage renal disease is currently being treated effectively by transplantation. However, increasing demand and donor shortage make this treatment challenging. Recent advances in cell-based therapies have provided potential opportunities to alleviate the current challenges of donor shortage. We previously have demonstrated that single renal cells expanded in culture are able to form renal structures when implanted in vivo. However, the levels of structure formation could not be adequately controlled. In this study, we investigated whether human kidney structures could be pre-formed in vitro for subsequent implantation in vivo to maximize tissue forming efficiency.

Primary human renal cells were isolated from unused donor kidneys using enzymatic digestion methods. Renal cells were grown, expanded and characterized using cell specific antibodies. To form kidney structures, single renal cells were placed in a three-dimensional culture system, consisting of neutralized type I collagen. The three-dimensional matrix with cells was solidified and cultivated over a period of 10 days. Histomorphological and ultrastructural analyses were performed using cell specific markers that identify proximal and distal tubules and collecting ducts.

Human primary renal cells were effectively isolated and expanded in culture. The cells retained their phenotypic and functional characteristics at multiple culture stages. Single renal cells placed in a three-dimensional culture environment began to proliferate and form structures that resemble renal tubules. Histologically, these structures showed phenotypic resemblance to native kidney structures. The reconstituted tubules stained positively for proximal and distal tubular markers. E-cadherin and N-cadherin staining confirmed polarization of the cells present in the tubules.

These findings show that single human renal cells grown in a three-dimensional culture system are able to generate kidney structures. The cells constituting these structures maintained the expression of renal cell specific markers. This system may ultimately be developed into an efficient cell-based therapy for patients with end stage renal disease.

Example 11

In Vivo Implantation of Reconstituted of Human Kidney Structures

Primary human renal cells were isolated from unused donor kidneys using enzymatic digestion methods. Renal cells were grown, expanded and characterized by immunocytochemistry and western blot using cell specific antibodies: proximal tubules: neprilysin (NEP); collecting duct: Tamm-Horsfall protein (THP); podocytes: podocin (POD). The ability of these cells to migrate was analyzed using different growth factors.

To form kidney structures, single renal cells were placed in a three-dimensional culture system of neutralized type I collagen. Histomorphological and ultrastructural analyses were performed using cell specific markers that identify proximal and distal tubules and collecting ducts. Albumin uptake assay was used to analyze the functionality of these tubules.

Human primary renal cells were effectively isolated and expanded in culture (FIG. 23). The cells retained their phenotypic characteristics, migration and albumin uptake functions (FIG. 24).

Renal cells placed in a three-dimensional culture environment began to proliferate and form structures that resemble renal tubules. Immunocytochemistry showed that the reconstituted renal structures were positive for expression of erythropoietin (EPO), Neprilysin (NEP) (proximal tubules), Tamm-Horsfall protein (THP) (collecting duct), and Podocin (POD) markers in passages 1, 2 and 3. Western blot analysis confirmed the presence of these protein markers. E-cadherin, N-cadherin and Na—K ATPase staining confirmed polarization of the cells present in the tubules. Co-localization of labeled albumin and tubule markers (including epithelia membrane antigen (EMA), which is a distal tubule marker) proved functionality and specificity of the new formed tubules. (FIG. 25)

3D cultures were implanted in the kidney of nude rats to evaluate survival of the cells (GFP cells) over a period of 6 weeks. The formed structures stained positively for anti-GFP after 3 weeks of implantation. Human kidney cells showed evidence of migration towards native tissue after 6 weeks of implantation in the interstitium area and in glomeruli.

These findings demonstrate that human renal cells grown in a three-dimensional culture system are able to generate kidney structures. The cells maintained the expression of renal cell specific markers and retained function. This system may ultimately be developed into an efficient cell-based therapy for patients with kidney disease.

The foregoing is illustrative of the present invention, and is not to be construed as limiting thereof. The invention is defined by the following claims, with equivalents of the claims to be included therein.

That which is claimed is:

1. A method of treating a kidney disease in a patient in need thereof, said method comprising:
   providing a composition comprising an isolated population of differentiated mammalian kidney cells comprising peritubular interstitial cells, wherein said cells are harvested from differentiated cells of a mammalian kidney tissue, passaged in vitro from 2 to 9 times, and seeded onto a three dimensional matrix, wherein (i) the cells of said population produce erythropoietin (EPO) under normoxic conditions, and (ii) the differentiated cells of the mammalian kidney tissue or the population of cells have not been manipulated by the introduction of an exogenous gene that stimulates the production of EPO or by an exogenous chemical that stimulates the production of EPO; and
   administering said composition to said patient in an amount effective to treat said kidney disease by surgically implanting said composition subcutaneously or into the kidney of said patient,
   to thereby treat said kidney disease in said patient in need thereof.

2. The method of claim 1, wherein said cells are positive for a marker selected from the group consisting of: neprilysin (NEP), Tamm-Horsfall protein (THP), podocin (POD), and combinations thereof, after said passaging.

3. The method of claim 1, wherein said population consists essentially of said differentiated mammalian kidney cells.

4. The method of claim 1, subject to the proviso that said cells are not transfected with an exogenous DNA encoding a polypeptide.

5. The method of claim 1, wherein said cells are human.

6. The method of claim 1, wherein said matrix comprises neutralized collagen type I.

7. The method of claim 1, wherein said kidney disease is an anemia selected from the group consisting of: an anemia of renal failure, an anemia of end-stage renal disease, an anemia of a chemotherapy, an anemia of a radiation therapy, an anemia of chronic infection, an anemia of an autoimmune disease, an anemia of rheumatoid arthritis, an anemia of AIDS, an anemia of a malignancy, an anemia of prematurity, an anemia of hypothyroidism, an anemia of malnutrition, and an anemia of a blood disorder.

8. The method of claim 7, wherein said anemia is an anemia of renal failure.

9. The method of claim 7, wherein said anemia is an anemia of end-stage renal disease.

10. The method of claim 1, wherein the matrix comprises a gel.

11. The method of claim 10, wherein the gel is a hydrogel.

12. The method of claim 10, wherein the gel is solidified.

13. The method of claim 1, wherein at least 40% or more of the cells of said population produce erythropoietin (EPO).

14. The method of claim 1, wherein at least 20% or more of the cells of said population produce erythropoietin (EPO).

15. The method of claim 1, wherein said kidney disease results in decreased EPO production in a patient, and wherein said cells produce EPO in vivo.

16. The method of claim 1, wherein said cells are syngeneic with respect to the patient.

17. The method of claim 1, wherein said cells are autogeneic with respect to the patient.

18. The method of claim 1, wherein the three dimensional matrix is biodegradable, and the population is provided in a treatment-effective amount.

19. The method of claim 1, wherein said differentiated mammalian kidney cells have been passaged in vitro from 2 to 6 times.

* * * * *